United States Patent
Short

(10) Patent No.: US 6,168,919 B1
(45) Date of Patent: *Jan. 2, 2001

(54) SCREENING METHODS FOR ENZYMES AND ENZYME KITS

(75) Inventor: Jay M. Short, Encinitas, CA (US)

(73) Assignee: Diversa Corporation, San Diego, CA (US)

( * ) Notice: Under 35 U.S.C. 154(b), the term of this patent shall be extended for 0 days.

This patent is subject to a terminal disclaimer.

(21) Appl. No.: 08/983,367

(22) PCT Filed: Jul. 17, 1996

(86) PCT No.: PCT/US96/11854

§ 371 Date: Sep. 30, 1998

§ 102(e) Date: Sep. 30, 1998

(87) PCT Pub. No.: WO97/04077

PCT Pub. Date: Feb. 6, 1997

(51) Int. Cl.⁷ .............................. C12Q 1/68; C12Q 1/00; C12P 19/34; C12N 15/64

(52) U.S. Cl. .................................. 435/6; 435/4; 435/91.1; 435/91.4; 435/91.41; 435/252.3; 435/183; 435/320.1; 435/325; 536/23.1; 536/23.2; 536/23.4

(58) Field of Search ................................. 435/4, 6, 91.1, 435/91.4, 91.41, 252.3, 183, 320.1, 325; 536/23.1, 23.2, 23.4

(56) References Cited

U.S. PATENT DOCUMENTS 5,171,684 * 12/1992 Yen et al. .......................... 435/252.3
5,712,146 * 1/1998 Khosla et al. .................. 435/252.35
5,958,672 * 9/1999 Short .......................................... 435/4

OTHER PUBLICATIONS

Lactic Dehydrogenase, Sigma catalog, p. 634, 1997.*

Anderson et al., Met. Enzymol., vol. 68, pp. 428–436, 1979.*

Promega Catalog, p. 205, 1993.*

Sambrook et al., Molecular Cloning, Cold Spring Harbor Laboratory Press, vol. 2, p. 9.30 and pp. 12.1–12.20, 1989.*

* cited by examiner

Primary Examiner—Ponnathapu Achutamurthy
Assistant Examiner—Peter P. Tung
(74) Attorney, Agent, or Firm—Gray, Cary, Ware & Freidenrich LLP; Lisa A. Haile

(57) ABSTRACT

Recombinant enzyme libraries and kits where a plurality of enzymes are each characterized by different physical and/or chemical characteristics and classified by common characteristics. The characteristics are determined by screening of recombinant enzymes expressed by a DNA library produced from various microorganisms. Also disclosed is a process for identifying clones of a recombinant library which express a protein with a desired ctivity by screening a library of expression clones randomly produced from DNA of at least one microorganism, said screeing being effected on expression products of said clones to thereby identify clones which express a protein with a desired activity. Also disclosed is a process of screening clones having DNA from an uncultivated microorganism for a specified protein activity by screening for a specified protein activity in a library of clones prepared by (I) recovering DNA from a DNA population derived from at least one uncultivated microorganism; and (ii) transforming a host with recovered DNA to produce a library of clones which is screened for the specified protein activity.

9 Claims, 6 Drawing Sheets

1. Concentrate bacteria, digest protein and preserve MW DNA

2. Partially digest DNA and select 40 kbp fragments by PFGE or by λ- packaging (step 3)

3. Ligate to fosmid arms, package and transfect to E. coli. Array library in microtiter plates.

SCREENING METHODS FOR ENZYMES AND ENZYME KITS

This invention relates to the field of preparing and screening libraries of clones containing microbially derived DNA and to protein, e.g. enzyme libraries and kits produced therefrom. More particularly, the present invention is directed to recombinant enzyme expression libraries, recombinant enzyme libraries and kits prepared therefrom which recombinant enzymes are generated from DNA obtained from microorganisms.

Industry has recognized the need for new enzymes for a wide variety of industrial applications. As a result, a variety of microorganisms have been screened to ascertain whether or not such microorganisms have a desired enzyme activity. If such microorganism does have a desired enzyme activity, the enzyme is then recovered from the microorganism.

Naturally occurring assemblages of microorganisms often encompass a bewildering array of physiological and metabolic diversity. In fact, it has been estimated that to date less than one percent of the world's organisms have been cultured. It has been suggested that a large fraction of this diversity thus far has been unrecognized due to difficulties in enriching and isolating microorganisms in pure culture. Therefore, it has been difficult or impossible to identify or isolate valuable enzymes from these samples. These limitations suggest the need for alternative approaches to characterize the physiological and metabolic potential i.e. activities of interest of as-yet uncultivated microorganisms, which to date have been characterized solely by analyses of PCR amplified rRNA Rene fragments, clonally recovered from mixed assemblage nucleic acids.

In accordance with one aspect of the present invention, there is provided a novel approach for obtaining enzymes for further use, for example, for packaging into kits for further research. In accordance with the present invention, recombinant enzymes are generated from microorganisms and are classified by various enzyme characteristics. In this manner, the enzymes can be provided as packaged enzyme screening kits, with enzymes in the kit being grouped to have selected enzyme characteristics.

More particularly, in accordance with this aspect of the present invention there is provided a recombinant expression library which is comprised of a multiplicity of clones which are capable of expressing recombinant enzymes. The expression library is produced by recovering DNA from a microorganism, cloning such DNA into an appropriate expression vector which is then used to transfect or transform an appropriate host for expression of a recombinant protein.

Thus, for example, genomic DNA may be recovered from either a culturable or non-culturable organism and employed to produce an appropriate recombinant expression library for subsequent determination of enzyme activity.

In accordance with an aspect of the present invention, such recombinant expression library may be prepared without prescreening the organism from which the library is prepared for enzyme activity.

Having prepared a multiplicity of recombinant expression clones from DNA isolated from an organism, the polypeptides expressed by such clones are screened for enzyme activity and specified enzyme characteristics in order to identify and classify the recombinant clones which produce polypeptides having specified enzyme characteristics.

In one aspect, the invention provides a process of screening clones having DNA from an uncultivated microorganism for a specified protein, e.g. enzyme, activity which process comprises:

screenings for a specified protein, e.g. enzyme, activity in a library of clones prepared by
  (i) recovering DNA from a DNA population derived from at least one uncultivated microorganism, and
  (ii) transforming a host with recovered DNA to produce a library of clones which are screened for the specified protein, e.g. enzyme, activity.

The library is produced from DNA which is recovered without culturing of an organism, particularly where the DNA is recovered from an environmental sample containing microorcanisms which are not or cannot be cultured.

In a preferred embodiment of this aspect DNA is ligated into a vector. particularly wherein the vector further comprises expression regulatory sequences which can control and regulate the production of a detectable enzyme activity from the ligated DNA.

The f-factor (or fertility factor) in *E. coli* is a plasmid which effects high frequency transfer of itself during conjugation and less frequent transfer of the bacterial chromosome itself. To archive and stably propogate large DNA fragments from mixed microbial samples, a particularly preferred embodiment is to use a cloning vector containing an f-factor origin of replication to generate genomic libraries that can be replicated with a high degree of fidelity. When integrated with DNA from a mixed uncultured environmental sample, this makes it possible to achieve large genomic fragments in the form of a stable "environmental DNA library."

In another preferred embodiment, double stranded DNA obtained from the uncultivated DNA population is selected by:
  converting the double stranded genomic DNA into single stranded DNA;
  recovering from the converted single stranded DNA single stranded DNA which specifically binds, such as by hybridization, to a probe DNA sequence; and
  converting recovered single stranded DNA to double stranded DNA.

The probe may be directly or indirectly bound to a solid phase by which it is separated from single stranded DNA which is not hybridized or otherwise specifically bound to the probe.

The process can also include releasing single stranded DNA from said probe after recovering said hybridized or otherwise bound single stranded DNA and amplifying the single stranded DNA so released prior to converting it to double stranded DNA.

The invention also provides a process of screening clones having DNA from an uncultivated microorganisms for a specified protein, e.g. enzyme, activity which comprises screening for a specified gene cluster protein product activity in the library of clones prepared by: (i) recovering DNA from a DNA population derived from at least one uncultivated microorganism; and (ii) transforming a host with recovered DNA to produce a library of clones with the screens for the specified protein, e.g. enzyme, activity. The library is produced from gene cluster DNA which is recovered without culturing of an organism, particularly where the DNA gene clusters are recovered from an environmental sample containing microorganisms which are not or cannot be cultured.

Alternatively, double-stranded gene cluster DNA obtained from the uncultivated DNA population is selected by converting the double-stranded genomic gene cluster DNA into single-stranded DNA; recovering from the converted single-stranded gene cluster polycistron DNA, single-stranded DNA which specifically binds, such as by hybridization, to a polynucleotide probe sequence; and converting recovered single-stranded gene cluster DNA to double-stranded DNA.

These and other aspects of the present invention are described with respect to particular preferred embodiments and will be apparent to those skilled in the art from the teachings herein.

DETAILED DESCRIPTION OF PREFERRED EMBODIMENTS

Figure 1:
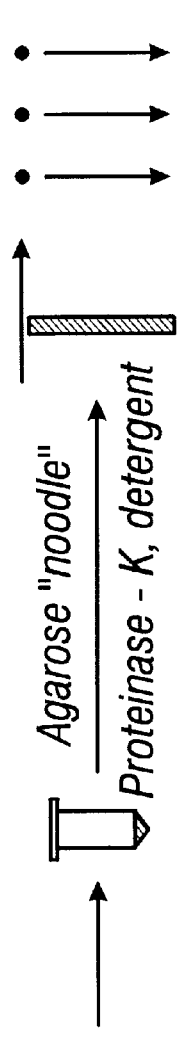
FIG. 1 shows an overview of the procedures used to construct an environmental library from a mixed picoplankton sample as described in Example 3.
Figure 1:
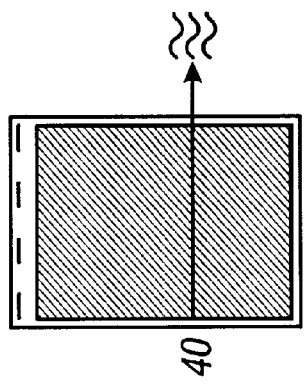
Figure 1:
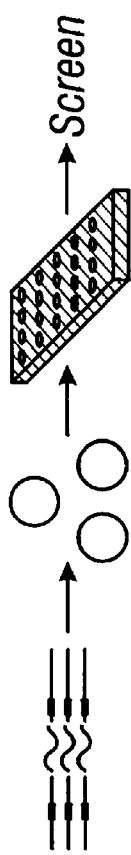

In accordance with a preferred aspect of the present invention, the recombinant enzymes are characterized by both physical and chemical characteristics and such chemical characteristics are preferably classified in a tiered manner such that recombinant enzymes having a chemical characteristic in common are then classified by other chemical characteristics which may or may not be more selective or specific chemical characteristic and so on, as hereinafter indicated in more detail.

As hereinabove indicated, the recombinant enzymes are also preferably classified by physical characteristics and one or more tiers of the enzymes which are classified by chemical characteristics may also be classified by physical characteristics or vice versa.

As used herein, the term "chemical characteristic" of a recombinant enzyme refers to the substrate or chemical functionality upon which the enzyme acts and/or the catalytic reaction performed by the enzyme; e.g., the catalytic reaction may be hydrolysis (hydrolases) and the chemical functionality may be the type of bond upon which the enzyme acts (esterases cleave ester bonds) or may be the particular type of structure upon which the enzyme acts (a glycosidase which acts on glycosidic bonds). Thus, for example, a recombinant enzyme which acts on glycosidic bonds may, for example, be chemically classified in accordance with the tiered system as: Tier 1: hydrolase; Tier 2: acetal bonds; Tier 3: glycosidase.

As used herein, a "physical characteristic" with respect to a recombinant enzyme means a property (other than a chemical reaction) such as pH; temperature stability; optimum temperature for catalytic reaction; organic solvent tolerance; metal ion selectivity; deterrent sensitivity; etc.

In an embodiment of the invention, in which a tiered approach is employed for classifying the recombinant enzymes by chemical and/or physical characteristics, the enzymes at one or more of the chemical characteristic tiers may also be classified by one or more physical characteristics and vice versa. In a preferred embodiment, the enzymes are classified by both physical and chemical characteristics, e.g., the individual substrates upon which they act as well as physical characteristics.

Thus, for example, as a representative example of the manner in which a recombinant enzyme may be classified in accordance with the present invention, a recombinant enzyme which is a protease (in this illustration Tier 1 is hydrolase; Tier 2 is amide (peptide bond) that may be further classified in Tier 3 as to the ultimate site in the amino acid sequence where cleavage occurs; e.g., anion, cation, large hydrophobic, small hydrophobic. Each of the recombinant enzymes which has been classified by the side chain in Tier 3 may also be further classified by physical characteristics of the type hereinabove indicated.

In this manner, it is possible to select from the recombinant library, enzymes which have a specified chemical characteristic in common, e.g., all endopeptidases (which act on internal peptide bonds) and which have a specified physical characteristic in common, e.g., all act optimally at a pH within a specified range.

As hereinabove indicated, a recombinant enzyme library prepared from a microorganism is preferably classified by chemical characteristics in a tiered approach. This may be accomplished by initially testing the recombinant polypeptides generated by the library in a low selectivity screen, e.g., the catalytic reaction performed by the enzyme. This may be conveniently accomplished by screening for one or more of the six IUB classes; Oxidoreductases; transferases; hydrolases, lyases, isomerases, ligases.

The recombinant enzymes which are determined to be positive for one or more of the IUB classes may then be rescreened for a more specific enzyme activity.

Thus, for example, if the recombinant library is screened for hydrolase activity, then those recombinant clones which are positive for hydrolase activity may be rescreened for a more specialized hydrolase activity, i.e., the type of bond on which the hydrolase acts. Thus, for example, the recombinant enzymes which are hydrolases may be rescreened to ascertain those hydrolases which act on one or more specified chemical functionalities, such as: (a) amide (peptide bonds), i.e., proteases: (b) ester bonds, i.e. esterases and lipases; (c) acetals, i.e., glycosidases, etc.

The recombinant enzymes which have been classified by the chemical bond on which they act may then be rescreened to determine a more specialized activity therefor, such as the type of substrate on which they act.

Thus, for example, those recombinant enzymes which have been classified as acting on ester bonds (lipases and esterases) may be rescreened to determine the ability thereof to generate optically active compounds, i.e., the ability to act on specified substrates, such as meso alcohols, meso diacids, chiral alcohols, chiral acids, etc.

For example, the recombinant enzymes which have been classified as acting on acetals may be rescreened to classify such recombinant enzymes by a specific type of substrate upon which they act, e.g., (a) P1 sugar such as glucose, galactose, etc., (b) glucose polymer (exo-, endo- or both), etc.

Enzyme Tiers

Thus, as a representative but not limiting example, the following are representative enzyme tiers:

TIER 1. Divisions are based upon the catalytic reaction performed by the enzyme, e.g., hydrolysis, reduction, oxidation, etc. The six IUB classes will be used: Oxidoreductase. Transferases, Hydrolases, Lyases, Isomerases, Ligases.

TIER 2: Divisions are based upon the chemical functionality undergoing reaction. e.g., esters, amides, phosphate diesters, sulfate mono esters, aldehydes, ketones, alcohols, acetals, ketals, alkanes, olefins, aromatic rings, heteroaromatic rings, molecular oxygen, enols, etc.

Lipases and esterases both cleave the ester bond, the distinction comes in whether the natural substrate is aggregated into a membrane (lipases) or dispersed into solution (esterases).

TIER 3: Divisions and subdivisions are based upon the differences between individual substrate structures which are covalently attached to the functionality undergoing reaction as defined in Tier 2. For example acetal hvdrolysis: is the acetal part of glucose or galactose: or is the acetal the α or β anomer? These are the types of distinctions made in TIER 3. The divisions based upon substrate specificity are unique to each particular enzyme reaction; there will be different substrate distinctions depending upon whether the enzyme is, for example, a protease or phosphatase.

TIER 4: Divisions are based on which of the two possible enantiomeric products the enzyme produces. This is a measure of the ability of the enzyme to selectively react with one of the two enantiomers (kinetic resolution), or the ability of the enzyme to react with a meso difunctional compound to selectively generate one of the two enantiomeric reaction products.

Tier 5/Orthogonal Tier/Physical Character Tier.

The fifth tier is orthogonal to the other tiers. It is based on the physical properties of the enzymes, rather than the chemical reactions, per se: The fifth Tier forms a second dimension with which to classify the enzymes. The Fifth Tier can be applied to any of the other Tiers, but will most often be applied to the Third Tier.

Thus, in accordance with an aspect of the present invention, an expression library is randomly produced from the DNA of a microorganism, in particular, the genomic DNA or cDNA of the microorganism and the recombinant proteins or polypeptides produced by such expression library are screened to classify the recombinant enzymes by different enzyme characteristics. In a preferred embodiment, the recombinant proteins are screened for one or more particular chemical characteristics and the enzymes identified as having such characteristics are then rescreened for a more specific chemical characteristic and this rescreening may be repeated one or more times. In addition, in a preferred embodiment, the recombinant enzymes are also screened to classify such enzymes by one or more physical characteristics. In this manner, the recombinant enzymes generated from the DNA of a microorganism are classified by both chemical and physical characteristics and it is therefore possible to select recombinant enzymes from one or more different organisms that have one or more common chemical characteristics and/or one or more common physical characteristics. Moreover, since such enzymes are recombinant enzymes, it is possible to produce such enzymes in desired quantities and with a desired purity.

The tiered approach of the present invention is not limited to a tiered approach in which, for example, the tiers are more restrictive. For example, the tiered approach is also applicable to using a tiered approach in which, for example, the first tier is "wood degrading" enzymes. The second chemical tier could then, for example, be the type of enzyme which is a "wood degrading" enzyme.

Similarly, the first tier or any other tier could be physical characteristics and the next tier could he specified chemical characteristics.

Thus, the present invention is generally applicable to providing recombinant enzymes and recombinant enzyme libraries wherein various enzymes are classified by different chemical and/or physical characteristics.

The microorganisms from which the recombinant libraries may be prepared include prokaryotic microorganisms, such as Eubacteria and Archaebacteria, and lower eukaryotic microorganisms such as fungi, some algae and protozoa. The microorganisms may be cultured microorganisms or uncultured microorganisms obtained from environmental samples and such microorganisms may be extremophiles, such as thermophiles, hyperthermophiles, psvchrophiles, psychrotrophs, etc.

Preferably, the library is produced from DNA which is recovered without culturing of an organism, particularly where the DNA is recovered from an environmental sample containing microorganisms which are not or cannot be cultured. Sources of microorganism DNA as a starting material library from which DNA is obtained are particularly contemplated to include environmental samples, such as microbial samples obtained from Arctic and Antarctic ice, water or permafrost sources, materials of volcanic origin, materials from soil or plant sources in tropical areas, etc. Thus, for example, genomic DNA may be recovered from either uncultured or non-culturable organism and employed to produce an appropriate library of clones for subsequent determination of enzyme activity.

Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered Penes are not necessarily identical. Gene clusters range from extremes where a duplication is generated to adjacent related genes to cases where hundreds of identical genes lie in a tandem —array. Sometimes no significance is discernable in a repetition of a particular gene. A principal example of this is the expressed duplicate insulin genes in some species, whereas a single insulin gene is adequate in other mammalian species.

It is important to further research gene clusters and the extent to which the full length of the cluster is necessary for the expression of the proteins resulting therefrom. Further, gene clusters undergo continual reorganization and, thus, the ability to create heterogeneous libraries of gene clusters from, for example, bacterial or other prokaryote sources is valuable in determining sources of novel proteins, particularly including proteins, e.g. enzymes, such as, for example, the polyketide synthases that are responsible for the synthesis of polyketides having a vast array of useful activities. Other types of proteins that are the product(s) of gene clusters are also contemplated, including, for example, antibiotics, antivirals, antitumor agents and regulatory proteins, such as insulin.

Polyketides are molcules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization. Polyketide synthase genes fall into gene clusters and at least one type (designated type 1) of polyketide syntheses have large size genes and enzymes, complicating genetic manipulation and in vitro studies of these genes/proteins.

The ability to select and combine desired components from a library of polyketide and postpolyketide biosynthesis genes for generation of novel polyketides for study is appealing. Using the method(s) of the present invention facilitates the cloning of novel polyketide synthases, particularly when one uses the f-factor based vectors, which facilitate cloning of gene clusters.

Preferably, the gene cluster DNA is ligated into a vector, particularly wherein a vector further comprises expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjuration and is ideal to achieve and stably propagate large DNA fragments, such as gene clusters from mixed microbial samples.

The term "derived" or "isolated" means that material is removed from its original environment (e.g. the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

As hereinabove indicated, the expression library may be produced from environmental samples in which case DNA may be recovered without culturing of an organism or the DNA may be recovered from a cultured organism.

In preparing the expression library genomic DNA may be recovered from either a cultured organism or an environmental sample (for example, soil) by various procedures. The recovered or isolated DNA is then fragmented into a size suitable for producing an expression library and for providing a reasonable probability that desired genes will be expressed and screened without the necessity of screening an excessive number of clones. Thus, for example, if the average genome fragment produced by shearing is 4.5 kbp, for a 1.8 Mbp genome about 2000 clones should be screened to achieve about a 90% probability of obtaining a particular gene. In some cases, in particular where the DNA is recovered without culturing, the DNA is amplified (for example by PCR) after shearing.

The sized DNA is cloned into an appropriate expression Vector and transformed into an appropriate host, preferably a bacterial host and in particular *E. coli*. Although *E. coli* is preferred, a wide variety of other hosts may be used for producing an expression library.

The expression vector which is used is preferably one which includes a promoter which is known to function in the selected host in case the native genomic promoter does not function in the host.

As representative examples of expression vectors which may be used for preparing an expression library, there may be mentioned phage, plasmids, phagemids, cosmids, phosmids, bacterial artificial chromosomes, P1-based artificial chromosomes, yeast artificial chromosomes, and any other vectors specific for specific hosts of interest (such as bacillus, aspergillus, yeast, etc.) The vector may also include a tag of a type known in the art to facilitate purification.

The following outlines a general procedure for producing expression libraries from both culturable and non-culturable organisms.

Culturable Organisms
Obtain Biomass
DNA Isolation (CTAB)
Shear DNA (25 gauge needle)
Blunt DNA (Mung Bean Nuclease)
Methylate (Eco RI Methylase)
Ligate to Eco RI linkers (GGAATTCC)
Cut back linkers (Eco RI Restriction Endonuclease)
Size Fractionate (Sucrose Gradient)
Ligate to lambda vector (Lambda ZAP II and gt11)
Package (in vitro lambda packaging extract)
Plate on *E. coli* host and amplify
Unculturable Organisms
Obtain cells
Isolate DNA (Various Methods)
Blunt DNA (Mung Bean Nuclease)
Ligate to adaptor containing a Not I site and conjugated to magnetic beads
Ligate unconjugated adaptor to the other end of the DNA
Amplify DNA in a reaction which allows for high fidelity, and uses adaptor sequences as primers
Cut DNA with Not I
Size fractionate (Sucrose Gradient or Sephacryl Column)
Ligate to lambda vector (Lambda ZAP II and gt11)
Package (in vitro lambda packaging extract)
Plate on *E. coli* host and amplify The probe DNA used for selectively recovering DNA of interest from the DNA derived from the at least one uncultured microorganism can be a full-length coding region sequence or a partial coding region sequence of DNA for an enzyme of known activity, a phylogenetic marker or other identified DNA sequence. The original DNA library can be preferably probed using mixtures of probes comprising at least a portion of the DNA sequence encoding the specified activity. These probes or probe libraries are preferably single-stranded and the microbial DNA which is probed has preferably been converted into single-stranded form. The probes that are particularly suitable are those derived from DNA encoding enzymes having an activity similar or identical to the specified enzyme activity which is to be screened.

The probe DNA should be at least about 10 bases and preferably at least 15 bases. In one embodiment, the entire coding region may be employed as a probe. Conditions for the hybridization in which DNA is selectively isolated by the use of at least one DNA probe will be designed to provide a hybridization stringency of at least about 50% sequence identity, more particularly a stringency providing for a sequence identity of at least about 70%.

Hybridization techniques for probing a microbial DNA library to isolate DNA of potential interest are well known in the art and any of those which are described in the literature are suitable for use herein, particularly those which use a solid phase-bound, directly or indirectly bound, probe DNA for ease in separation from the remainder of the DNA derived from the microorganisms.

Preferably the probe DNA is "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

The library of clones prepared as described above can be screened directly for a desired, e.g. enzymatic, activity without the need for culture expansion, amplification or other supplementary procedures. However, in one preferred embodiment, it is considered desirable to amplify the DNA recovered from the individual clones such as by PCR.

Further, it is optional but desirable to perform an amplification of the target DNA that has been isolated. In this embodiment the selectively isolated DNA is separated from the probe DNA after isolation. It is then amplified before being used to transform hosts. The double stranded DNA selected to include as at least a portion thereof a predetermined DNA sequence can be rendered single stranded, subjected to amplification and reannealed to provide amplified numbers of selected double stranded DNA. Numerous amplification methodologies are now well known in the art.

The selected DNA is then used for preparing a library for screening by transforming a suitable organism. Hosts, particularly those specifically identified herein as preferred, are transformed by artificial introduction of the vectors containing the target DNA by inoculation under conditions conducive for such transformation.

As representative examples of expression vectors which may be used there may be mentioned viral particles, baculovirus, phage, plasmids, phagemids, cosmids, phosmids, bacterial artificial chromosomes, viral DNA (e.g. vaccinia, adenovirus. foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example: Bacterial: pQE70, pQE60, pQE-9 (Qiagen), psiX174, pBluescript SK. pBluescript KS, pNH8A, pNH16a, pNH18A, pNH46A (Stratagene); pTRC99a, pKK223-3. pKK233-3, pDR540, pRIT5 (Pharmacia); Eukaryotic: pWLNEO, pSV2CAT. pOG44. pXT1, pSG (Stratagene) pSVK3. pBPV, pMSG. pSVL (Pharmacia). However, any other plasmid or vector may be used as long as they are replicable and viable in the host.

A particularly preferred type of vector for use in the present invention contains an f-factor origin of replication. The f-factor (or fertility factor) in E. coli is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from the E. coli f-factor and are able to stably integrate large segments of genomic DNA. When integrated with DNA from a mixed uncultured environmental sample, this makes it possible to achieve large genomic fragments in the form of a stable "environmental DNA library."

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. Particular named bacterial promoters include lac, lacZ. T3. T7. gpt, lambda $P_R$, $P_L$ and trp. Eukaryotic promoters include CMV immediate early. HSV thvmidine kinase, early and late SV40. LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Generally, recombinant expression vectors will include origins of replication and selectable markers permitting transformation of the host cell, e.g., the ampicillin resistance gene of E. coli and S. cerevisiae TRPI gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heteroiogous structural sequence is assembled in appropriate phase with translation initiation and termination sequences, and preferably, a leader sequence capable of directing secretion of translated protein into the periplasmic space or extracellular medium.

The DNA selected and isolated as hereinabove described is introduced into a suitable host to prepare a library which is screened for the desired enzyme activity. The selected DNA is preferably already in a vector which includes appropriate control sequences whereby selected DNA which encodes for an enzyme may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by transformation, calcium phosphate transfection, DEAE-Dextran mediated transfection, DMSO or electroporation (Davis, L., Dibner, M. Battey, I., Basic Methods in Molecular Biology, (1986)).

As representative examples of appropriate hosts, there may be mentioned: bacterial cells, such as E. coli. Bacillus, Streptomyces, *Salmonella typhimurium*; fungal cells, such as yeast; insect cells such as Drosophila S2 and Spodoptera Sf9; animal cells such as CHO. COS or Bowes melanoma: adenoviruses; plant cells, etc. The selection of an appropriate host is deemed to be within the scope of those skilled in the art from the teachings herein.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

The recombinant enzymes in the library which are classified as described herein may or may not be sequenced and may or may not be in a purified form. Thus, in accordance with the present invention, it is possible to classify one or more of the recombinant enzymes before or after obtaining the sequence of the enzyme or before or after purifying the enzyme to essential homogeneity.

The screening for chemical characteristics may be effected on individual expression clones or may be initially effected on a mixture of expression clones to ascertain whether or not the mixture has one or more specified enzyme activities. If the mixture has a specified enzyme activity, then the individual clones may be rescreened for such enzyme activity or for a more specific activity. Thus, for example, if a clone mixture has hydrolase activity, then the individual clones may be recovered and screened to determine which of such clones has hydrolase activity.

The present invention is also directed to preparing and providing enzyme kits for use in further screening and/or research. Thus, in accordance with an aspect of the invention, a reagent package or kit is prepared by placing in the kit or package, e.g., in suitable containers, at least three different recombinant enzymes with each of the at least three different recombinant enzymes having at least two enzyme characteristics in common. In a preferred embodiment, one common characteristic is a chemical characteristic or property and the other common characteristic is a physical characteristic or property; however, it is possible to prepare kits which have two or more chemical characteristics or properties in common and no physical characteristics or property in common and vice versa.

Since, in accordance with the present invention, it is possible to provide a recombinant enzyme library from one or more microorganisms which is classified by a multiplicity of chemical and/or physical properties, a variety of enzyme kits or packages can be prepared having a variety of selected chemical and/or physical characteristics which can be formulated to contain three or more recombinant enzymes in which at least three and preferably all of the recombinant enzymes have in common at least one chemical characteristic and have in common at least one physical characteristic. The kit should contain an appropriate label specifying such common characteristics.

In one embodiment, at least three recombinant enzymes in the kit have in common the most specific chemical characteristic specified on the label. The term "label" is used in its broadest sense and includes package inserts or literature associated or distributed in conjunction with the kit or package. Thus, for example, if the kit is labeled for a specific substrate (one of the Tier 3 examples above), then for example, at least three of the enzymes in the kit would act on such substrate.

The kits will preferably contain more than three enzymes, for example, five, six or more enzymes and in a preferred embodiment at least three and preferably a majority and in some cases all of the recombinant enzymes in the kit will have at least two enzyme properties or characteristics in common, as hereinabove described.

The recombinant enzymes in the kits may have two or more enzymes in a single container or individual enzymes in individual containers or various combinations thereof.

The library may be screened for a specified enzyme activity by procedures known in the art. For example, the enzyme activity may be screened for one or more of the six IUB classes; oxidoreductases, transferases, hydrolases, lyases, isomerases and ligases. The recombinant enzymes which are deter-mined to be positive for one or more of the IUB classes may then be rescreened for a more specific enzyme activity.

Alternatively, the library may be screened for a more specialized enzyme activity. For example, instead of generically screening for hydrolase activity, the library may be screened for a more specialized activity, i.e. the type of bond on which the hydrolase acts. Thus, for example, the library may be screened to ascertain those hydrolases which act on one or more specified chemical functionalities, such as: (a) amide (peptide bonds), i.e. proteases: (b) ester bonds, i.e. esterases and lipases; (c) acetals, i.e., glycosidases etc.

The clones which are identified as having the specified enzyme activity may then be sequenced to identify the DNA sequence encoding an enzyme having the specified activity. Thus, in accordance with the present invention it is possible to isolate and identify: (i) DNA encoding an enzyme having a specified enzyme activity, (ii) enzymes having such activity (inlcuding the amino acid sequence thereof) and (iii) produce recombinant enzymes having such activity.

The screening for enzyme activity may be effected on individual expression clones or may be initially effected on a mixture of expression clones to ascertain whether or not the mixture has one or more specified enzyme activities. If the mixture has a specified enzyme activity, then the individual clones may be rescreened for such enzyme activity or for a more specific activity. Thus, for example, if a clone mixture has hydrolase activity, then the individual clones may be recovered and screened to determine which of such clones has hydrolase activity.

The expression libraries may be screened for one or more selected chemical characteristics. Selected representative chemical characteristics are described below but such characteristics do not limit the present invention. Moreover, the expression libraries may be screened for some or all of the characteristics. Thus, some of the chemical characteristics specified herein may be determined in all of the libraries, none of the libraries or in only some of the libraries.

The recombinant enzymes may also be tested and classified by physical properties. For example, the recombinant enzymes may be classified by physical properties such as follows:

pH optima
<3
3–6
6–9
9–12
>12 temperature optima
>90° C.
75–90° C.
60–75° C.
45–60° C.
30–45° C.

15–30° C.
0–15° C.
temperature stability
  half-life at:
  90° C.
  75° C.
  60° C.
  45° C.
organic solvent tolerance
  water miscible
  (DMF)
  90%
  75%
  45%
  30%
  water immiscible
  hexane
  toluene
metal ion selectivity
  EDTA—10 mM
  $Ca^{+2}$—1 mM
  $Mg^{+2}$—100 μM
  $Mn^{+2}$—10 μM
  $Co^{+3}$—10 μM
detergent sensitivity
  neutral (triton)
  anionic (deoxycholate)
  cationic (CHAPS)

The recombinant enzymes of the libraries and kits of the present invention may be used for a variety of purposes and the present invention by providing a plurality of recombinant enzymes classified by a plurality of different enzyme characteristics permits rapid screening of enzymes for a variety of applications. Thus, for example, the present invention permits assembly of enzyme kits which contain a plurality of enzymes which are capable of operating on a specific bond or a specific substrate at specified conditions to thereby enable screening of enzymes for a variety of applications. As representative examples of such applications, there may be mentioned:

1. Lipase/Esterase
    a. Enantioselective hydrolysis of esters (lipids) thioesters
        1) Resolution of racemic mixtures
        2) Synthesis of optically active acids or alcohols from meso-diesters
    b. Selective syntheses
        1) Regiospecific hydrolysis of carbohydrate esters
        2) Selective hydrolysis of cyclic secondary alcohols
    c. Synthesis of optically active esters, lactones, acids, alcohols
        1) Transesterification of activated/nonactivated esters
        2) Interesterification
        3) Optically active lactones from hydroxyesters
        4) Regio- and enantioselective ring opening of anhydrides
    d. Detergents
    e. Fat/Oil conversion
    f. Cheese ripening
2. Protease
    a. Ester/amide synthesis
    b. Peptide synthesis
    c. Resolution of racemic mixtures of amino acid esters
    d. Synthesis of non-natural amino acids
    e. Detergents/protein hydrolysis
3. Glycosidase/Glycosyl transferase
    a. Sugar/polymer synthesis
    b. Cleavage of glycosidic linkages to form mono, di-and oligosaccharides
    c. Synthesis of complex oligosaccharides
    d. Glycoside synthesis using UDP-galactosyl transferase
    e. Transglycosylation of disaccharides, glycosyl fluorides, aryl galactosides
    f. Glycosyl transfer in oligosaccharide synthesis
    g. Diastereoselective cleavage of β-glucosylsulfoxides
    h. Asymmetric glycosylations
    i. Food processing
    j. Paper processing
4. Phosphatase/Kinase
    a. Synthesis/hydrolysis of phosphate esters
        1) Regio-, enantioselective phosphorylation
        2) Introduction of phosphate esters
        3) Synthesize phospholipid precursors
        4) Controlled polynucleotide synthesis
    b. Activate biological molecule
    c. Selective phosphate bond formation without protecting groups
5. Mono/Dioxygenase
    a. Direct oxyfunctionalization of unactivated organic substrates
    b. Hydroxidation of alkane, aromatics, steroids
    c. Epoxidation of alkenes
    d. Enantioselective sulphoxidation
    e. Regio- and stereoselective Bayer-Villiger oxidations
6. Haloperoxidase
    a. Oxidative addition of halide ion to nucleophilic sites
    b. Addition of hypohalous acids to olefinic bonds
    c. Ring cleavage of cyclopropanes
    d. Activated aromatic substrates converted to ortho and para derivatives
    e. 1.3 diketones converted to 2-halo-derivatives
    f. Heteroatom oxidation of sulfur and nitrogen containing substrates
    g. Oxidation of enol acetates, alkynes and activated aromatic rinsrs
7. Lignin peroxidase/Diarylpropane peroxidase
    a. Oxidative cleavage of C—C bonds
    b. Oxidation of benzylic alcohols to aldehydes
    c. Hydroxylation of benzylic carbons
    d. Phenol dimerization
    e. Hydroxylation of double bonds to form diols
    f. Cleavage of lignin aldehydes
8. Epoxide hydrolase
    a. Synthesis of enantiomerically pure bioactive compounds
    b. Regio- and enantioselective hydrolysis of epoxide
    c. Aromatic and olefinic epoxidation by monooxygenases to form epoxides
    d. Resolution of racemic epoxides
    e. Hydrolysis of steroid epoxides
9. Nitrile hydratase/nitrilase
    a. Hydrolysis of aliphatic nitrites to carboxamides b. Hydrolysis of aromatic, heterocyclic, unsaturated aliphatic nitriles to corresponding acids
c. Hydrolysis of acrylonitrile
d. Production of aromatic and carboxamides, carboxylic acids (nicotinamide, picolinamide, isonicotinamide)
e. Regioselective hydrolysis of acrylic dinitrile
f. α-amino acids from c-hydroxynitriles
10. Transaminase
   a. Transfer of amino groups into oxo-acids
11. Amidase/Acylase
   a. Hydrolysis of amides, amidines, and other C-N bonds
   b. Non-natural amino acid resolution and synthesis The invention will be further described with reference to the following examples; however, the scope of the present invention is not to be limited thereby. Unless otherwise specified, all parts are by weight.

EXAMPLE 1

Production of Expression Library

The following describes a representative procedure for preparing an expression library for screening by the tiered approach of the present invention.

One gram of Thermococcus GU5L5 cell pellet was lysed and the DNA isolated by literature procedures (Current Protocols in Molecular Biology, 2,4,1, 1987). Approximately 100 μg of the isolated DNA was resuspended in TE buffer and vigorously passed through a 25 gauge double-hubbed needle until the sheared fragments were in the size range of 0.5–10.0 Kb (3.0 Kb average). The DNA ends were "polished" or blunted with Mung Bean Nuclease (300 units, 37° C., 15 minutes), and EcoRI restriction sites in the target DNA protected with EcoRI Methylase (200 units, 37° C., 1 hour). EcoRI linkers [GGAATTCC] were ligated to the blunted/protected DNA using 10 pmole ends of linkers to 1 pmole end of target DNA. The linkers were cut back with EcoRI restriction endonuclease (200 units, 37° C., 1.5 hours) and the DNA size fractionated by sucrose gradient (Maniatis, T., Fritsch, E. F., and Sambrook, J., *Molecular Cloning*, Cold Spring Harbor Press, New York, 1982). The prepared target DNA was ligated to the Lambda ZAP® II vector (Stratagene). packaged using in vitro lambda packaging extracts and grown on XLI-Blue MRF' *E. coli* strain according to the manufacturer. The pBluescript® phagemids were excised from the lambda library, and crown in *E. coli* DH10B F' kan, according to the method of Hay and Short (Hay and Short. *J. Strategies*, 5:16, 1992). The resultin2 colonies were picked with sterile toothpicks and used to singly inoculate each of the wells of 11 96-well microtiter plates (1056 clones in all). The wells contained 250 μL of LB media with 100 μg/mL ampicillin. 80 μg/mL methicillin, and 10% v/v glycerol (LB Amp/Meth, glycerol). The cells were grown overnight at 37° C. without shaking. This constituted generation of the "Source Library"; each well of the Source Library thus contained a stock culture of *E. coli* cells, each of which contained a pBluescript phagemid with a unique DNA insert.

EXAMPLE 2

Preparation of a Mammalian DNA Library

The following outlines the procedures used to generate a gene library from a sample of the exterior surface of a whale bone found at 1240 meters depth in the Santa Catalina Basin during a dive expedition.

Isolate DNA.
IsoQuick Procedure as per manufacturer's instructions.
Shear DNA
1. Vigorously push and pull DNA through a 25 G double-hub needle and 1-cc syringes about 500 times.
2. Check a small amount (0.5 μg) on a 0.8% agarose gel to make sure the majority of the DNA is in the desired size range (about 3–6 kb).

Blunt DNA
1. Add:
   $H_2O$ to a final volume of 405 μl
   45 μl 10× Mung Bean Buffer
   2.0 μl Mung Bean Nuclease (150 μ/μl)
2. Incubate 37° C., 15 minutes.
3. Phenol/chloroform extract once.
4. Chloroform extract once.
5. Add 1 ml ice cold ethanol to precipitate.
6. Place on ice for 10 minutes.
7. Spin in microfuge, high speed, 30 minutes.
8. Wash with 1 ml 70% ethanol.
9. Spin in microftige, high speed, 10 minutes and dry.

Methylate DNA
1. Gently resuspend DNA in 26 μl TE.
2. Add:
   4.0 μl 10× EcoR I Methylase Buffer
   0.5 μl SAM (32 mM)
   5.0 μl EcoR I Methylase (40 μ/μl)
3. Incubate 37°, 1 hour.

Insure Blunt Ends
1. Add to the methylation reaction:
   5.0 μl 100 mM $MgCl_2$
   8.0 μl dNTP mix (2.5 mM of each dGTP, dATP, dTTP, dCTP)
   4.0 μl Klenow (5 μ/μl)
2. Incubate 12° C., 30 minutes.
3. Add 450 μl 1× STE.
4. Phenol/chloroforrn extract once.
5. Chlorotorm extract once.
6. Add 1 ml ice cold ethanol to precipitate and place on ice for 10 minutes.
7. Spin in microfupe, high speed. 30 minutes.
8. Wash with 1 ml 70% ethanol.
9. Spin in microfuge, high speed, 10 minutes and dry.

Linker Ligation
1. Gently resuspend DNA in 7 μl Tris-EDTA (TE).
2. Add:
   14 μl Phosphorylated EcoR I linkers (200 ng/μl)
   3.0 μl 10× Lication Buffer
   3.0 μl 10 mM rATP
   3.0 μl T4 DNA Ligase (4 Wu/μl)
3. Incubate 4° C., overnight.

EcoRI Cutback
1. Heat kill ligation reaction 68° C. 10 minutes.
2. Add:
   237.9 μl $H_2O$
   30 μl 10× EcoR I Buffer
   2.1 μl EcoR I Restriction Enzyme (100 u/μl)
3. Incubate 37° C., 1.5 hours.
4. Add 1.5 μl 0.5 M EDTA.
5. Place on ice.

Sucrose Gradient (2.2 ml) Size Fractionation

1. Heat sample to 65° C., 10 minutes.
2. Gently load on 2.2 ml sucrose gradient.
3. Spin in mini-ultracentrifuge, 45K. 20° C. 4 hours (no brake).
4. Collect fractions by puncturing the bottom of the gradient tube with a 20 G needle and allowing the sucrose to flow through the needle. Collect the first 20 drops in a Falcon 2059 tube then collect 10 1-drop fractions (labelled 1–10). Each drop is about 60 µl in volume.
5. Run 5 µl of each fraction on a 0.8% agarose gel to check the size.
6. Pool fractions 1–4 (~10–1.5 kb) and, in a separate tube, pool fractions 5–7 (about 5–0.5 kb).
7. Add 1 mil ice cold ethanol to precipitate and place on ice for 10 minutes.
8. Spin in microfuge, high speed, 30 minutes.
9. Wash with 1 ml 70% ethanol.
10. Spin in microfuge, high speed, 10 minutes and dry.
11. Resuspend each in 10 µl TE buffer.

Test Ligation to Lambda Arms

1. Plate assay to get an approximate concentration. Spot 0.5 µl of the sample on agarose containing ethidium bromide along with standards (DNA samples of known concentration). View in UV light and estimate concentration compared to the standards. Fraction 1–4=>1.0 µg/µl. Fraction 5–7=500 ng/µl.
2. Prepare the following ligation reactions (5 µl reactions) and incubate 4° C. overnight:

| Sample | H₂O | 10X Ligase Buffer | 10 mM rATP | Lambda arms (gt11 and ZAP) | Insert DNA | T4 DNA Ligase (4 Wu/µ) |
|---|---|---|---|---|---|---|
| Fraction 1–4 | 0.5 µl | 0.5 µl | 0.5 µl | 1.0 µl | 2.0 µl | 0.5 µl |
| Fraction 5–7 | 0.5 µl | 0.5 µl | 0.5 µl | 1.0 µl | 2.0 µl | 0.5 µl |

Test Package and Plate

1. Package the ligation reactions following manufacturer's protocol. Package 2.5 µl per packaging extract (2 extracts per ligation).
2. Stop packaging reactions with 500 µl SM buffer and pool packaging that came from the same ligation.
3. Titer 1.0 µl of each on appropriate host (OD$_{600}$=1.0) [XLI-Blue MRF for ZAP and Y1088 for gt11]
   Add 200 µl host (in mM MgSO$_4$) to Falcon 2059 tubes
   Inoculate with 1 µl packaged phage
   Incubate 37° C., 15 minutes
   Add about 3 ml 48° C. top agar
     [50 ml stock containing 150 µl IPTG (0.5M) and 300 µl X-GAL (350 mg/ml)]
   Plate on 100 mm plates and incubate 37° C., overnight.
4. Efficiency results:
   gt11: 1.7×10$^4$ recombinants with 95% background
   ZAP II: 4.2×10$^4$ recombinants with 66% background Contaminants in the DNA sample may have inhibited the enzymatic reactions, though the sucrose gradient and organic extractions may have removed them. Since the DNA sample was precious, an effort was made to "fix" the ends for cloning:

Re-Blunt DNA

1. Pool all left over DNA that was not ligated to the lambda arms (Fractions 1–7) and add H$_2$O to a final volume of 12 µl. Then add:
   143 µl H$_2$O
   20 µl 10× Buffer 2 (from Stratagene's cDNA Synthesis Kit)
   23 µl Blunting dNTP (from Stratagene's cDNA Synthesis Kit)
   2.0 µl Pfu (from Stratagene's cDNA Synthesis Kit)
2. Incubate 72° C., 30 minutes.
3. Phenol/chloroform extract once.
4. Chloroform extract once.
5. Add 20 µL 3M NaOAc and 400 µl ice cold ethanol to precipitate.
6. Place at −20° C., overnight.
7. Spin in microfuge, high speed. 30 minutes.
8. Wash with 1 ml 70% ethanol.
9. Spin in microfuge, high speed, 10 minutes and dry.

(Do NOT Methylate DNA since it was already methylated in the first round of processing)

Adaptor Ligation

1. Gently resuspend DNA in 8 µl EcoR I adaptors (from Stratagene's cDNA Synthesis Kit).
2. Add:
   1.0 µl 10× Ligation Buffer
   1.0 µl 10 mM rATP
   1.0 µl T4 DNA Ligase (4 Wu/µl)
3. Incubate 4° C. 2 days.

(Do NOT cutback since using ADAPTORS this time. Instead, need to phosphorylate)

Phosphorylate Adaptors

1. Heat kill ligation reaction 70° C. 30 minutes.
   Add:
   1.0 µl 10× Ligation Buffer
   2.0 µl 10 mM rATF
   6.0 µl H$_2$O
   1.0 µl PNK (from Stratagene's cDNA Synthesis Kit).
3. Incubate 37° C., 30 minutes.
4. Add 31 µl H$_2$O and 5 µl 10× STE.
5. Size fractionate on a Sephacryl S-500 spin column (pool fractions 1–3).
6. Phenol/chloroform extract once.
7. Chloroform extract once.
8. Add ice cold ethanol to precipitate.
9. Place on ice, 10 minutes.
10. Spin in microfuge, high speed, 30 minutes.
11. Wash with 1 ml 70% ethanol.
12. Spin in microfuge, high speed. 10 minutes and dry.
13. Resuspend in 10.5 µl TE buffer.

Do not plate assay. Instead, ligate directly to arms as above except use 2.5 µl of DNA and no water.

Package and titer as above.

Efficiency results:
   gt11: 2.5×10$^6$ recombinants with 2.5% background
   ZAP II: 9.6×10$^5$ recombinants with 0% background Amplification of Libraries (5.0×10$^5$ recombinants from each library)

1. Add 3.0 ml host cells (OD$_{600}$=1.0) to two 50 ml conical tube.
2. Inoculate with 2.5×10$^5$ pfu per conical tube.
3. Incubate 37° C. 20 minutes.
4. Add top agar to each tube to a final volume of 45 ml.
5. Plate the tube across five 150 mm plates.
6. Incubate 37° C., 6–8 hours or until plaques are about pin-head in size.

7. Overlay with 8–10 ml SM Buffer and place at 4° C. overnight (with gentle rocking if possible).

Harvest Phage

1. Recover phage suspension by pouring the SM buffer off each plate into a 50-ml conical tube.
2. Add 3 ml chloroform, shake vigorously and incubate at room temperature, 15 minutes.
3. Centrifuge at 2K rpm, 10 minutes to remove cell debris.
4. Pour supernatant into a sterile flask, add 500 µl chloroform.
5. Store at 4° C.

Titer Amplified Library

1. Make serial dilutions:
   $10^{-5}$=1 µl amplified phage in 1 ml SM Buffer
   $10^{-5}$=1 µl of the $10^{-3}$ dilution in 1 ml SM Buffer
2. Add 200 µl host (in 10 mM $MgSO_4$) to two tubes.
3. Inoculate one with 10 µl $10^{-6}$ dilution ($10^{-5}$).
4. Inoculate the other with 1 µl $10^{-6}$ dilution ($10^{-6}$).
5. Incubate 37° C., 15 minutes.
6. Add about 3 ml 48° C. top agar.
   [50 ml stock containing 150 µl IPTG (0.5M) and 375 µl X-GAL (350 mg/ml)]
7. Plate on 100 mm plates and incubate 37° C., overnight.
8. Results:
   gt11: $1.7 \times 10^{11}$/ml
   ZAP II: $2.0 \times 10^{10}$/ml Excise the ZAP II library to create the pBluescript library.

EXAMPLE 3

Preparation of an Uncultivated Prokaryotic DNA Library

FIG. 1 shows an overview of the procedures used to construct an environmental library from a mixed picoplankton sample. The goal was to construct a stable, large insert DNA library representing picoplankton genomic DNA.

Cell collection and preparation of DNA. Agarose plugs containing concentrated picoplankton cells were prepared from samples collected on an oceanographic cruise from Newport, Oreg. to Honolulu. Hi. Seawater (30 liters) was collected in Niskin bottles, screened through 10 µm Nitex, and concentrated by hollow fiber filtration (Amicon DC10) through 30.000 MW cutoff polysulfone filters. The concentrated bacterioplankton cells were collected on a 0.22 µm, 47 mm Durapore filter, and resuspended in 1 ml of 2× STE buffer (IM NaCl, 0.1M EDTA, 10 mM Tris, pH 8.0) to a final density of approximately $1 \times 10^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10mM Tris pH 8.0, 50 mM NaCl, 0.1M EDTA. 1% Sarkosyl, 0.2% sodium deoxycholate, a mg/ml lysozyme) and incubated at 37° C. for one hour. The agarose plug was then transferred to 40 mis of ESP Buffer (1% Sarkosyl, 1 mg/ml proteinase-K. in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 µl) prepared from a sample collected off the Oregon coast was dialyzed overnight at 4° C. against 1 mL of buffer A (100 mM NaCl, 10 mM Bis Tris Propane-HCl, 100 µg/ml acetylated BSA: pH 7.0@25° C.) in a 2 mL microcentrifuge tube. The solution was replaced with 250 µl of fresh buffer A containing 10 mM $MgCl_2$ and 1 mM DTT and incubated on a rocking platform for 1 hr at room temperature. The solution was then changed to 250 µl of the same buffer containing 4U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the protein, e.g. enzyme, and to melt the agarose. The agarose was digested and the DNA dephosphorylased using Gelase and HK-phosphalase (Epicentre). respectively, according to the manufacturer's recornmendations. Protein was removed by gentle phenol/chloroformn extraction and the DNA was ethanol precipitated, pelleted, and then washed with 70% ethanol. This partially digested DNA was resuspended in sterile $H_2O$ to a concentration of 2.5 ng/µl for ligation to the pFOS1 vector.

PCR amplification results from several of the agarose plugs (data not shown) indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., high abundance of Archaea in Antarctic marine picoplankton, Nature, 371:695–698, 1994). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately $7.5 \times 10^{-5}$ cells, therefore approximately $5.4 \times 10^5$ cells were present in the 72 µl slice used in the preparation of the partially digested DNA.

Vector arms were prepared from pFOS1 as described (Kim et al. Stable propagation of casmid sized human DNA inserts in an F factor based vector. Nucl. Acids Res., 20.10832–10835, 1992). Briefly, the plasmid was completely digested with AstII. dephosphorylated with HK phosphatase, and then digested with BamHI to generate two arms, each of which contained a cos site in the proper orientation for cloning and packaging ligated DNA between 35–45 kbp. The partially digested picoplankton DNA was ligated overnight to the PFOS1 arms in a 15 µl ligation reaction containing 25 ng each of vector and insert and 1 U of T4 DNA ligase (Boehringer-Mannheim). The ligated DNA in four microliters of this reaction was in vitro packaged using the Gigapack XL packaging system (Stratagene), the fosmid particles transfected to E. coli strain DH10B (BRL). and the cells spread onto $LB_{cm15}$ plates. The resultant fosmid clones were picked into 96-well microliter dishes containing $LB_{cm15}$ supplemented with 7% glycerol. Recombinant fosmids, each containing ca. 40 kb of picoplankton DNA insert, yielded a library of 3.552 fosmid clones, containing approximately $1.4 \times 10^8$ base pairs of cloned DNA. All of the clones examined contained inserts ranging from 38 to 42 kbp. This library was stored frozen at −80° C. for later analysis.

EXAMPLE 4

Enzymatic Activity Assay

The following is a representative example of a procedure for screening an expression library prepared in accordance with Example 2. In the following, the chemical characteristic Tiers are as follows:

Tier 1: Hydrolase
Tier 2: Amide. Ester and Acetal
Tier 3: Divisions and subdivisions are based upon the differences between individual substrates which are covalently attached to the functionality of Tier 2 undergoing reaction: as well as substrate specificity.
Tier 4: The two possible enantiomeric products which the enzyme may produce from a substrate.

Although the following example is specifically directed to the above mentioned tiers, the general procedures for testing for various chemical characteristics is generally applicable to substrates other than those specifically referred to in this Example.

Screening for Tier 1-hydrolase: Tier 2-amide.

The eleven plates of the Source Library were used to multiply inoculate a single plate (the "Condensed Plate") containing in each well 200 μL of LB Amp/Meth, glycerol. This step was performed using the High Density Replicating Tool (HDRT) of the Beckman Biomek with a 1% bleach, water, isopropanol, air-dry sterilization cycle in between each inoculation. Each well of the Condensed Plate thus contained II different pBluescript clones from each of the eleven source library plates. The Condensed Plate was grown for 2 h at 37° C. and then used to inoculate two white 96-well Dynatech microtiter daughter plates containing in each well 250 μL of LB Amp/Meth, glycerol. The original condensed plates was incubated at 37° C. for 18 h then stored at –80° C. The two condensed daughter plates were incubated at 37° C. also for 18 h. The condensed daughter plates were then heated at 70° C. for 45 min. to kill the cells and inactivate the host $E.$ $coli$ enzymes. A stock solution of 5 mg/mL morphourea phenylalanyl-7-amino-4-trifluoromethyl coumarin (MuPheAFC, the 'substrate') in DMSO was diluted to 600 μM with 50 mM pH 7.5 Hepes buffer containing 0.6 mg/mL of the detergent dodecyl maltoside.

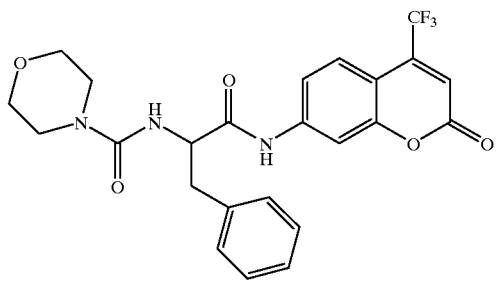

MuPheAFC

Fifty μL of the 600 μM MuPheAFC solution was added to each of the wells of the white condensed plates with one 100 μL mix cycle using the Biomek to yield a final concentration of substrate of ~100 μM. The fluorescence values were recorded (excitation=400 nm. emission=505 nm) on a plate reading fluorometer immediately after addition of the substrate (t=0). The plate was incubated at 70° C. for 100 min, then allowed to cool to ambient temperature for 15 additional minutes. The fluorescence values were recorded again (t=100). The values at t=0 were subtracted from the values at t=100 to determine if an active clone was present.

These data indicated that one of the eleven clones in well G8 was hydrolyzing the substrate. In order to determine the individual clone which carried the activity, the eleven source library plates were thawed and the individual clones used to singly inoculate a new plate containing LB Amp/Meth, glycerol. As above, the plate was incubated at 37° C. to grow the cells, heated at 70° C. to inactivate the host enzymes. and 50 μL of 600 μM MuPheAFC added using the Biomek. Additionally three other substrates were tested. The methyl umbelliferone heptanoate, the CBZ-arginine rhodamine derivative, and fluorescein-conjugated casein (3.2 mol fluorescein per mol of casein).

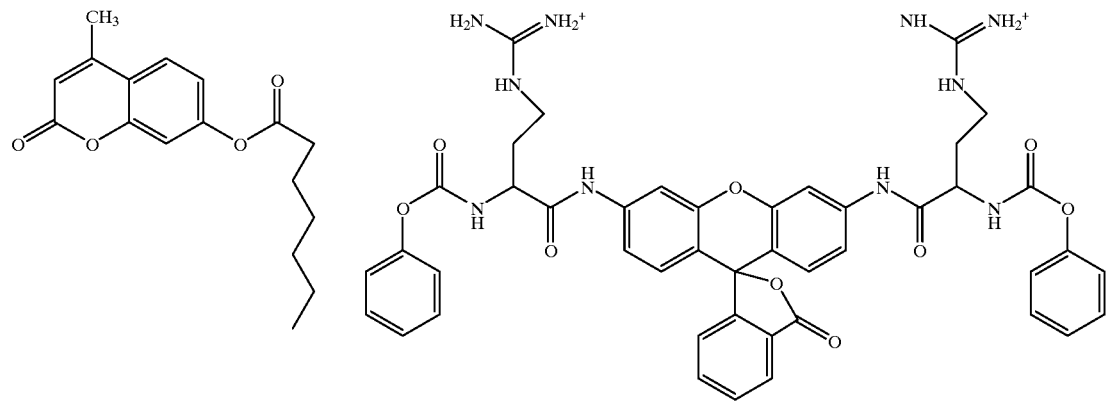

methyl umbelliferone heptanoate (CBZ-arginine)₂ rhodamine 110

The umbeliferone and rhodamine were added as 600 μM stock solutions in 50 μL of Hepes buffer. The fluorescein conjugated casein was also added in 50 μL at a stock concentration of 20 and 200 mg/mL. After addition of the substrates the t=0 fluoresence values were recorded, the plate incubated at 70° C., and the t=100 min. values recorded as above.

These data indicated that the active clone was in plate 2. The arginine rhodamine derivative was also turned over by this activity, but the lipase substrate, methyl umbelliferone heptanoate, and protein, fluorescein-conjugated casein, did not function as substrates.

Based on the above data the Tier 1 classification is hydrolase and the Tier 2 classification is amide bond. There is no cross reactivity with the Tier 2-ester classification.

Figure 2:
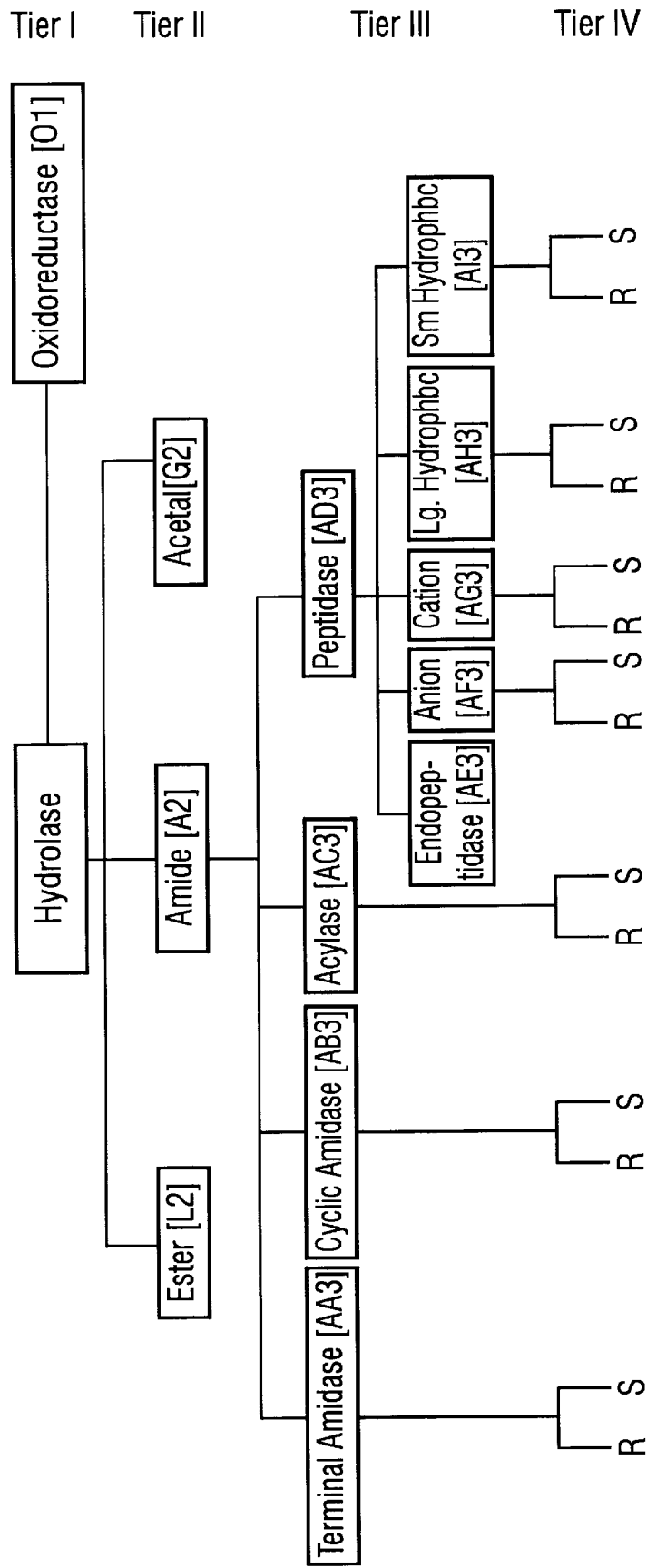
FIG. 2 is a schematic representation of one embodiment of various tiers of chemical characteristics of an enzyme which may be employed in the present invention as described in Example 4.

As shown in FIG. 2, a recombinant clone from the library which has been characterized in Tier 1 as hydrolase and in Tier 2 as amide may then be tested in Tier 3 for various specificities. In FIG. 2, the various classes of Tier 3 are followed by a parenthetical code which identifies the substrates of Table 1 which are used in identifying such specificities of Tier 3.

Figure 3:
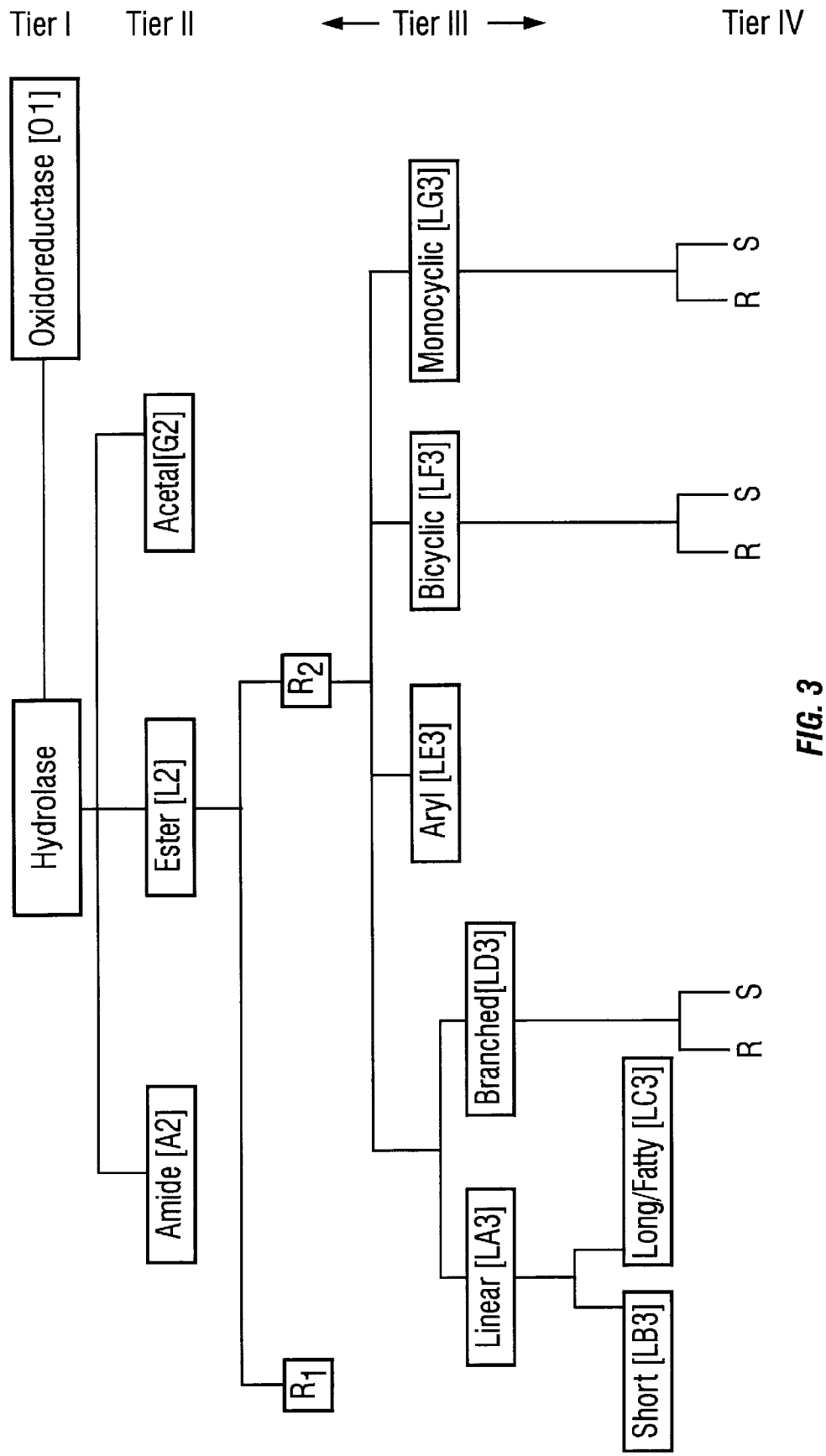
FIG. 3 is a schematic representation of another embodiment of various tiers of chemical characteristics of an enzyme which may be employed in the present invention as described in Example 4.
Figure 4:
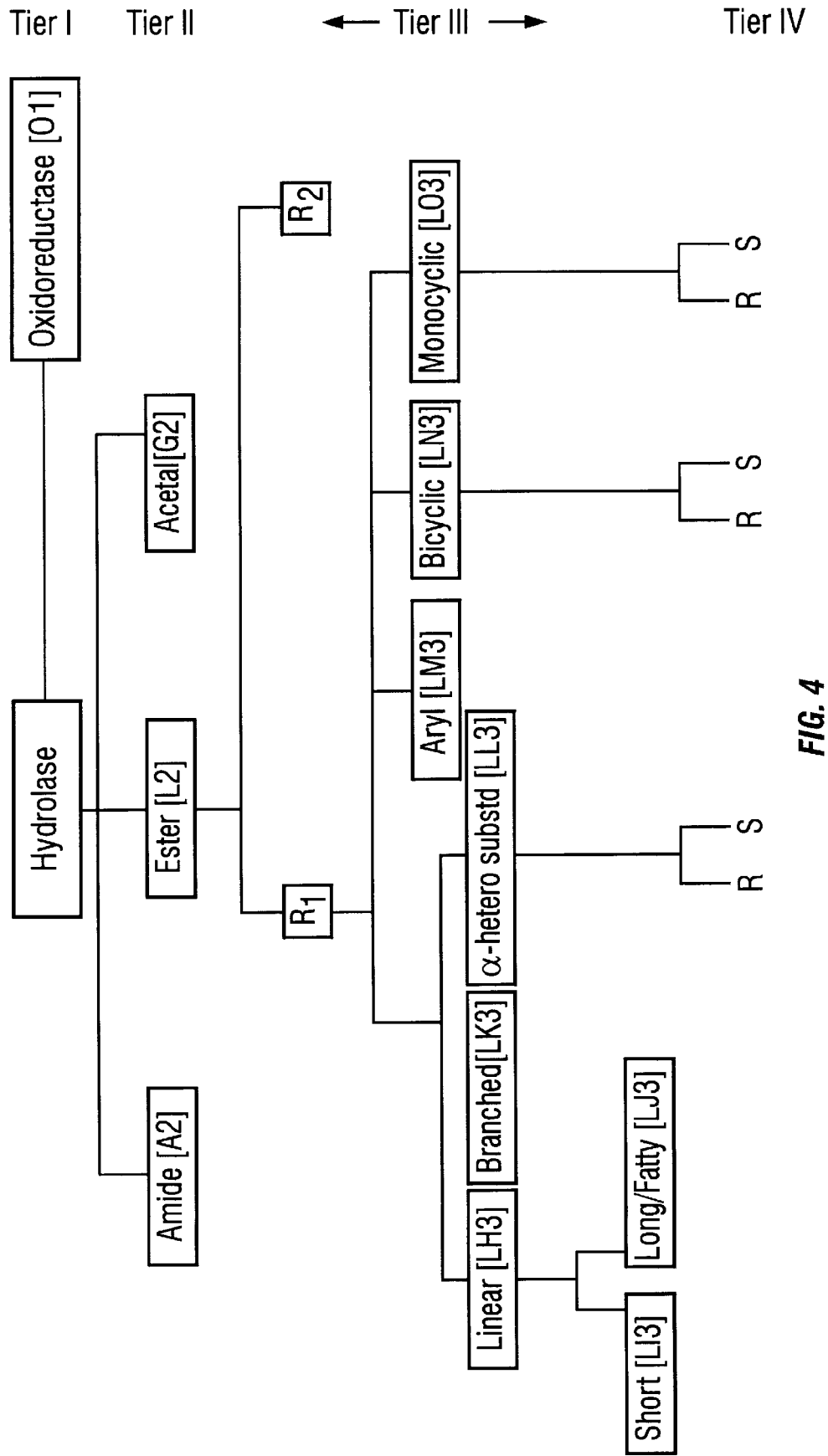
FIG. 4 is a schematic representation of a further embodiment of various tiers of chemical characteristics of an enzyme which may he employed in the present invention as described in Example 4.

As shown in FIGS. 3 and 4. a recombinant clone from the librarn which has been characterized in Tier 1 as hydrolase and in Tier 2 as ester may then be tested in Tier 3 for various specificities. In FIGS. 3 and 4, the various classes of Tier 3 are followed by a parenthetical code which identifies the substrates of Tables 2 and 2 which are used in identifying such specificities of Tier 3. In FIGS. 3 and 4, $R_2$ represents the alcohol portion of the ester and $R_1$ represents the acid portion of the ester.

Figure 5:
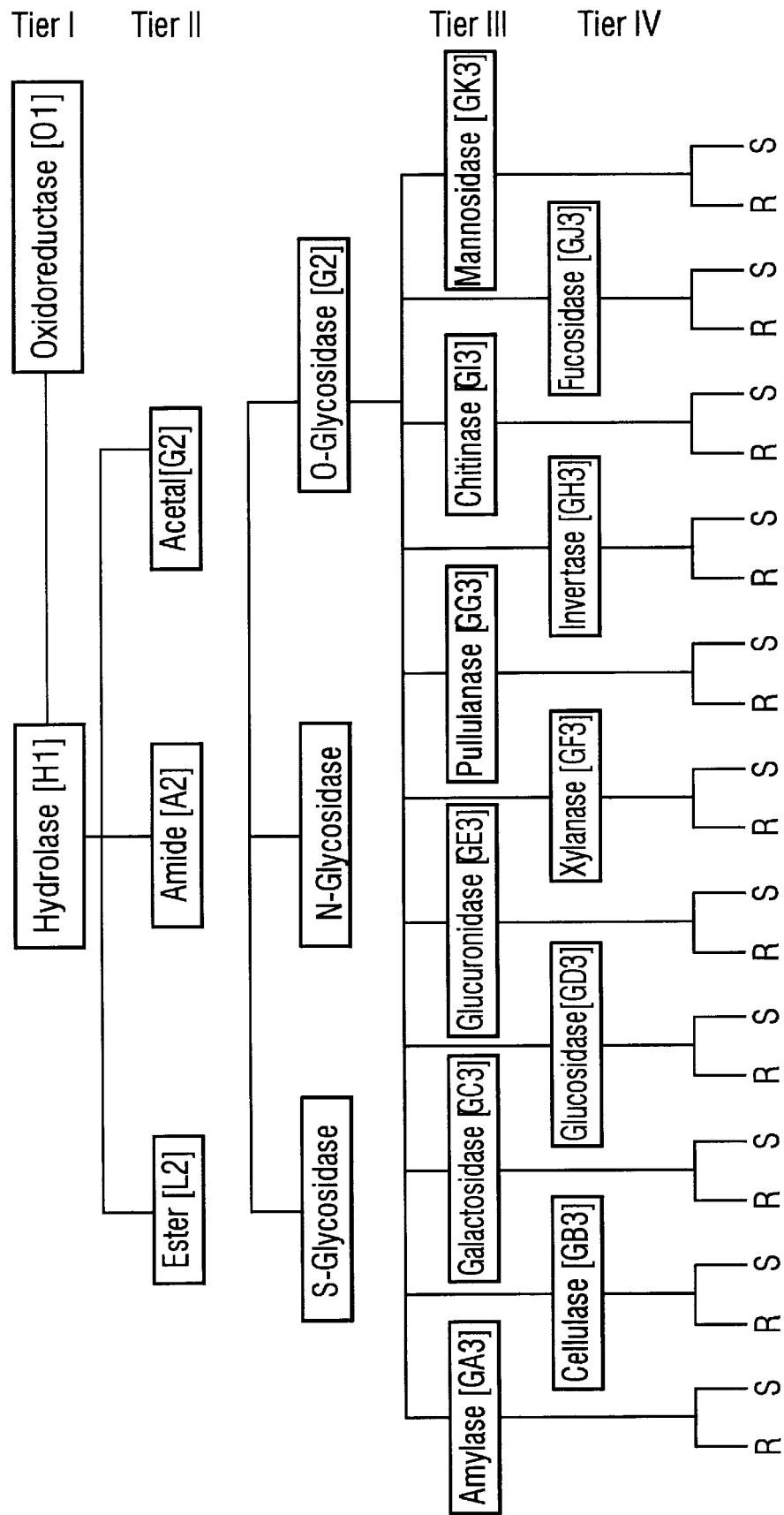
FIG. 5 is a schematic representation of a still further embodiment of various tiers of chemical characteristics of an enzyme which may be employed in the present invention as described in Example 4.

As shown in FIG. 5, a recombinant clone from the library which has been characterized in Tier 1 as hydrolase and in Tier 2 as acetal may then be tested in Tier 3 for various specificilies. In FIG. 5, the various classes of Tier 3 are followed by a parenthetical code which identifies the substrates of Table 4 which are used in identifying such specificities of Tier 3.

Enzymes may be classified in Tier 4 for the chirality of the product(s) produced by the enzyme. For example, chiral amino esters may be determined using at least the following substrates:

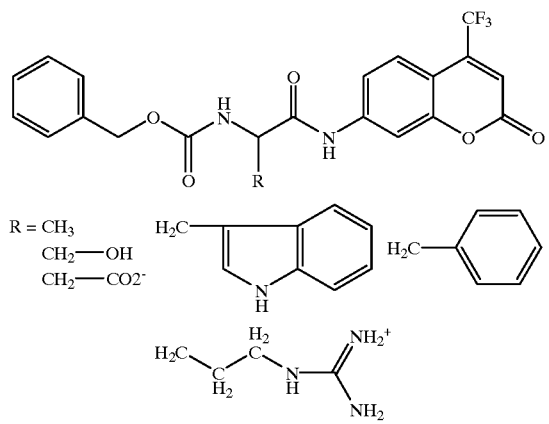

R = CH₃
CH₂—OH
CH₂—CO₂⁻

For each substrate which is turned over the enantioselectiviyt value, E, is determined according to the equation below:

$$E = \frac{\ln[(1 - c(1 + ee_p)]}{\ln[(1 - c(1 - ee_p)]}$$

where $ee_p$=the enantiomeric excess (ee) of the hydrolyzed product and c=the percent conversion of the reaction. See Wong and Whitesides. Enzymes in Synthetic Organic Chemistry, 1994. Elsevier, Tarrytown, N.Y., pgs. 9–12.

The enantiomeric excess is determined by either chiral high performance liquid chromatography (HPLC) or chiral capillary electrophoresis (CE). Assays are performed as follows: two hundred μL of the appropriate buffer is added to each well of a 96-well white microtiter plate, followed by 50 μL of partially or completely purified enzyme solution; 50 μL of substrate is added and the increase in fluorescence monitored versus time until 50% of the substrate is consumed or the reaction stops, which ever comes first.

Enantioselectivity was determined for one of the esterases identified as follows. For the reaction to form (transesterification) or breakdown (hydrolysis) α-methyl benzyl acetate, the enantioselectivity of the enzyme was obtained by determining: $ee_c$ (the enantiomeric excess (ee) of the unreacted substrate). $ee_p$ (the ee of the hydrolyzed product). and c (the percent conversion of the reaction). The enantiomeric excess was by determined chiral high performance gas chromatography (GC). Chromatography conditions were as follows:

Sample Preparation: Samples were filtered through a 0.2 μm, 13 mm diameter PTFE filter.

Column: Supelco β-DEX 120, 0.25 mm ID, 30 m, 0.25 μm $d_f$.

Oven: 90° C. for 1 min, then 90° C. to 150° C. at 5° C./min.

Carrier Gas: Helium, 1 mL/min for 2 min then 1 mL/min. to 3 mL/min at 0.2 mL/min.

Detector: FID, 300° C.

Injection: 1 μL (1 mM substrate in reaction solvent), split (1:75), 200° C.

The transesterification reaction was performed according to the procedure described in: *Organic solvent tolerance. Water immiscible solvents.* See below.

Transesterification with Enzyme ESL-001-01 gave the following results:

| Solvent   | % ee$_s$ | % ee$_p$ | % c  |
|-----------|----------|----------|------|
| n-heptane | 10.9     | 44.3     | 19.8 |
| toluene   | 3.2      | 100      | 3.1  |

The hydrolysis reaction was performed as follows: Fifty μL of a 10 mM solution of a-methyl benzyl acetate in 10% aqueous DMSO (v/v) was added to 200 μL of 100 mM, pH 6.9 phosphate buffer. To this solution was added 250 μL of Enzyme ESL-001-01 (2 mg/mL in 100 mM, pH 6.9 phosphate buffer) and the reaction heated at 70° C. for 15 min. The reaction was worked up according to the following procedure: remove 250 μL of hydrolysis reaction mixture and add to a 1 mL Eppendorf tube. Add 250 μL of ethyl acetate and shake vigorously for 30 seconds. Allow phases to separate for 15 minutes. Pipette off 200 μL of top organic phase and filter through a 0.2 μm. 4 mm diameter PTFE filter. Analyze by chiral GC as above.

Hydrolysis with Enzyme ESL-001-01 gave the following results:

| % ee$_s$ | % ee$_p$ | % c |
|---|---|---|
| 100 | 0.7 | 99.3 |

EXAMPLE 5

Testing for Physical Characteristics of a Recombinant Clone

This example describes procedures for testing for certain physical characteristics of a recombinant clone of a library.

pH optima.

Two hundred μL of 4-methyl-umbelliferyl-2,2-dimethyl-4-pentenoate was added to each well of a 96-well microtiter plate and serially diluted from column 1 to 12. Fifty μL of the appropriate 5× pH buffer was added to each row of the plate so that reaction rate in eight different pH's were tested on a single plate. Twenty μL of Enzyme ESL-001-01 (1:3000 dilution of a 1 mg/mL stock solution) was added to each well to initiate the reaction. The increase in absorbance at 370 nm at 70° C. was monitored to determine the rate of reaction; the rate versus substrate concentration fit to the Michaelis-Menten equation to determine $V_{MAX}$ at each pH.

Figure 6:
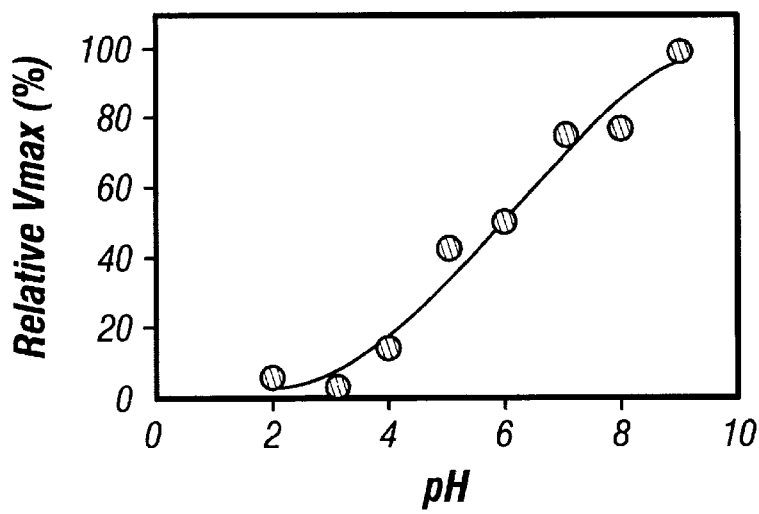
FIG. 6 shows the pH optima results produced by enzyme ESL-001-01 in the experiments described in Example 5.

Enzyme ESL-001-01 gave the results shown in FIG. 6.

Temperature optima.

To a one mL thermostatted cuvette was added 930 μL of 50 mM, pH 7.5 Hepes buffer. After temperature equilibration 50 μL of Enzyme ESL-001-01 (1:8000 dilution of a 1 mg/mL stock solution in Hepes buffer) and 20 μL of 5 mM 4-methyl-heptanoate containing 30 mg/mL dodecyl maltoside. The rate of increase in absorbance at 370 nm was measured at 10, 20, 30, 40, 50, 60, 70, 80, and 90° C.

Figure 7:
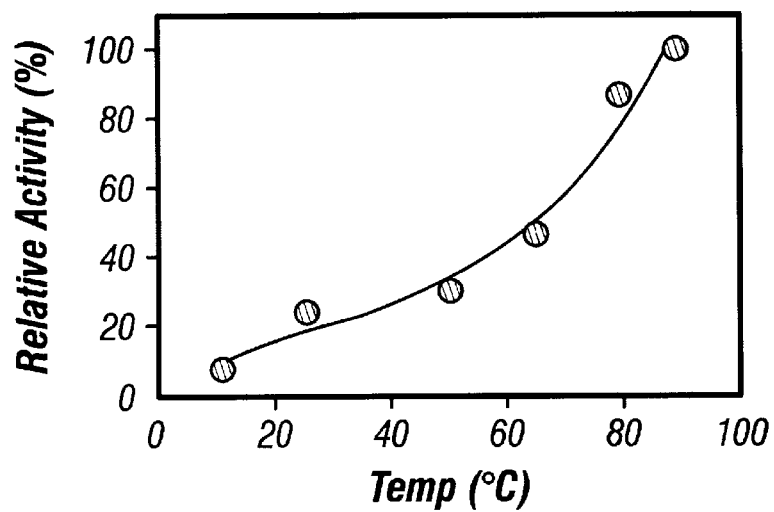
FIG. 7 shows the temperature optima results produced by enzyme ESL-001-01 in the experiments described in Example 5.

Enzyme ESL-001-01 gave the results shown in FIG. 7.

Temperature stability.

One mL samples of Enzyme ESL-001-01 (1:4000 dilution of a 1 mg/mL stock solution in Hepes buffer) were incubated at 70, 80, and 90° C. At selected time points 25 μL aliquots were removed and assayed as above in a 96 well microtiter plate with 200 μL of 100 μM 4-methylumbelliferyl palmitate and 0.6 mg/mL dodecyl maltoside. This data was used to determine the half life for inactivation of the enzyme.

Enzyme ESL-001-01 gave the following results:

| Temperature | Half Life |
|---|---|
| 90 | 23 min. |
| 80 | 32 min. |
| 70 | 110 h |

Organic solvent tolerance.

Water miscible solvents (dimethylsulfoxide (DMSO) and tetrahydro furan (THF)).

Thiryu μL of 1 mM 4-methyl-umbelliferyl-butyrate in the organic solvent was added to the wells of a 96-well microtiter plate. Two hundred forty μL of buffer and organic solvent mixture (see table below) were added the wells of the plate, followed by 30 μL of an Enzyme ESL-001-01 (1:50,000 dilution of a 1 mg/mL stock solution in 50 mM, pH 6.9 MOPS buffer) and incubation at 70° C. The increase in fluorescence (EX=360 nm, EM=440 nm) was monitored versus time to determine the relative activities.

| μL Organic Solvent | μL Buffer | % Organic Solvent Final |
|---|---|---|
| 240 | 0 | 90 |
| 195 | 45 | 75 |
| 150 | 90 | 60 |
| 120 | 120 | 50 |
| 90 | 150 | 40 |
| 60 | 180 | 30 |
| 30 | 210 | 20 |
| 0 | 240 | 10 |

Figure 8:
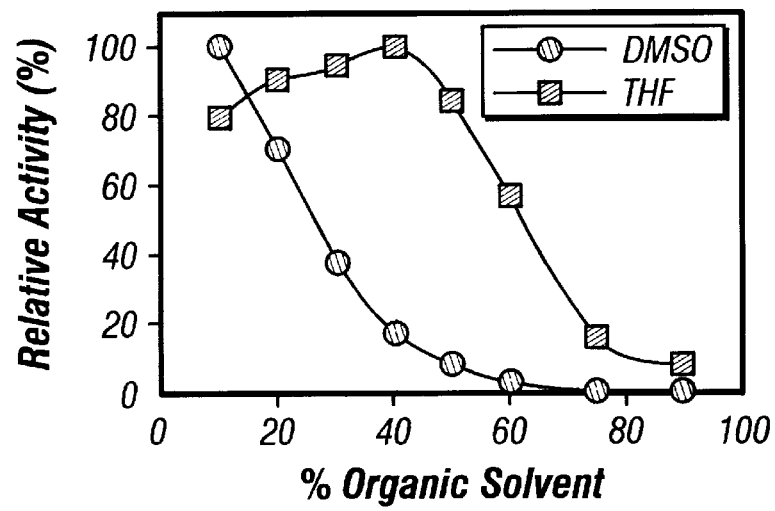
FIG. 8 shows the organic solvent tolerance results produced by enzyme ESL-001-01 in the experiments described in Example 5.

Enzyme ESL-001-01 Ol gave the results shown in FIG. 8.

Water immiscible solvents (n-heptane, toluene)

One mL of the solvent was added to a vial containing 1 mg of lyophilized Enzyme ESL-001-01 and a stir bar. Ten μL of 100 mM 1-phenethyl alcohol and 10 μL of 100 mM vinyl acetate were added to the vial and the vial stirred in a heating block at 70° C. for 24 h. The sample was filtered through a 0.2 μm. 4 mm diameter PTFE filter and analyzed by chiral GC as above. See previous section for data.

Specific Activity

The specific activity was determined using 100 μM 4-methyl umbelliferyl heptanoate at 90° C. in pH 6.9 MOPS buffer. The specific activity obtained for Enzyme ESL-001-01 was 1662 μmol/min·mg.

EXAMPLE 6

Testing for Substrate Specificity of a Recombinant Clone

This example describes procedures for testing for substrate specificity of a recombinant clone of a library.

Substrate Fingerprint.

One and one quarter millimolar solutions containing 1 mg/mL of dodecyl maltoside in 50 mM pH 6.9 MOPS buffer of each of the following substrates were prepared:

4-methyl umbelliferyl acetate (A)
 4-methyl umbelliferyl propanoate (B)
 4-methyl umbelliferyl2 butyrate (C)
 4-methyl umbelliferyl heptanoate (D)
 4-methyl umbelliferyl α-methyl butyrate (E)
 4-methyl umbelliferyl β-methylcrotonoate (F)
 4-methyl umbelliferyl 2,2-dimethyl -4-pentenoate (G)
 4-methyl umbelliferyl adipic acid monoester (H)
 4-methyl umbelliferyl 1,4-cycylohexane dicarboxylate (I)
 4-methyl umbelliferyl benzoate (M)
 4-methyl umbelliferyl p-trimethyl ammonium cinnamate (N)
 4-methyl umbelliferyl 4-muanidinobenzoate (O)
 4-methyl umbelliferyl α-methyl phenyl acetate (P)
 4-methyl umbelliferyNl α-methoxy phenyl acetate (Q)
 4-methyl umbelliferyl palmitate (S)
 4-methyl umbelliferyl stearale (T)
 4-methyl umbelliferyl oleate (U)
 4-methyl umbelliferyl elaidate (W).

Two hundred μL of each of the above solutions were added to the wells of a 96 well microtiter plate, followed by 50 μL of Enzyme ESL-001-01 (1:2000 dilution of a 1 mg/mL stock solution in MOPS buffer) and incubation at 70° C. for 20 min. The fluorescence (EX=360 nm, EM=440 nm) was measured and fluorescence due to nonenzymatic hydrolysis was subtracted. Table 5 shows the relative fluorescence of each of the above substrates.

Numerous modifications and variations of the present invention are possible in light of the above teachings, therefore, within the scope of the claims, the invention may be practiced other than as particularly described.

TABLE 1

A2

Fluorescen conjugated casein (3.2 mol fluorescein/mol casein)
CBZ-Ala-AMC
t-BOC-Ala-Ala-Asp-AMC
succinyl-Ala-Gly-Leu-AMC
CBZ-Arg-AMC
CBZ-Met-AMC
morphourea-Phe-AMC

AA3

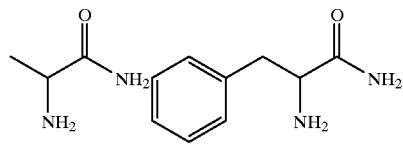

AB3

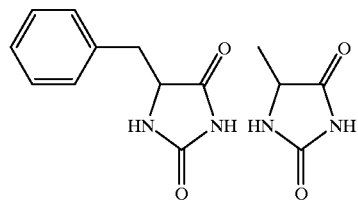

AC3

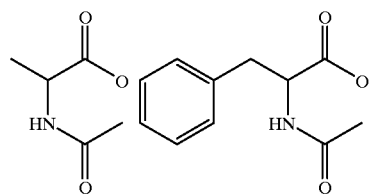

TABLE 1-continued

AD3

Fluorescein conjugated casein
t-BOC-Ala-Ala-Asp-AFC
CBZ-Ala-Ala-Lys-AFC
succinyl-Ala-Ala-Phe-AFC
succinyl-Ala-Gly-Leu-AFC

AE3

Fluoroscein conjugated casein

AF3 t-BOC-Ala-Ala-Asp-AFC
CBZ-Asp-AFC

AG3

CBZ-Ala-Ala-Lys-AFC
CBZ-Arg-AFC

AH3 succinyl-Ala-Ala-Phe-AFC
CBZ-Phe-AFC
CBZ-Trp-AFC

AI3 succinyl-Ala-Gly-Leu-AFC
CBZ-Ala-AFC
CBZ-Sewr-AFC t-BOC = t-butoxy carbony, CBZ carbonyl benzyloxy, AMC = 7-amino-4-methyl coumarin
AFC = 7-amino-4-trifluoromethyl coumarin.)

TABLE 2
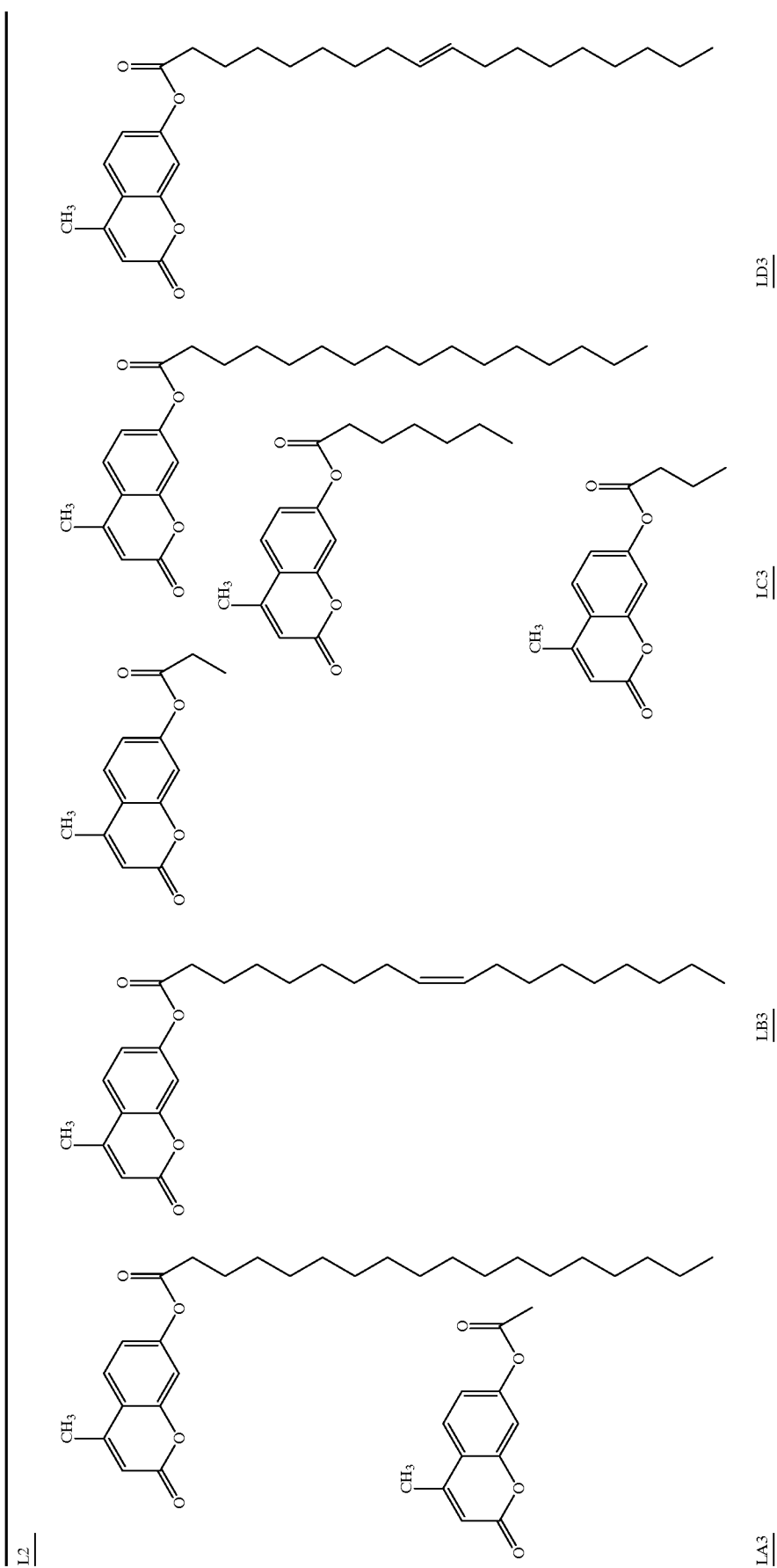

TABLE 2-continued
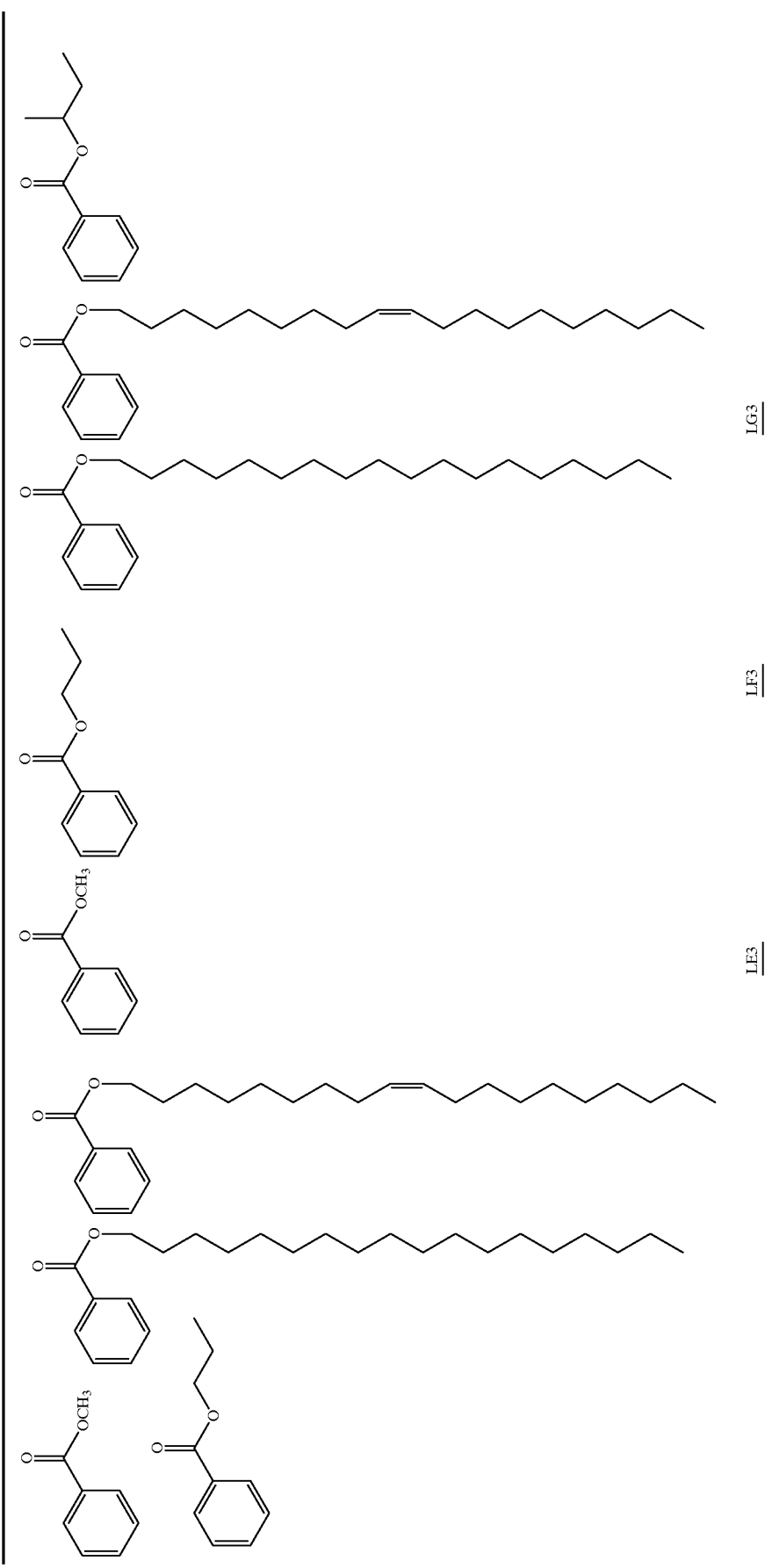

TABLE 2-continued
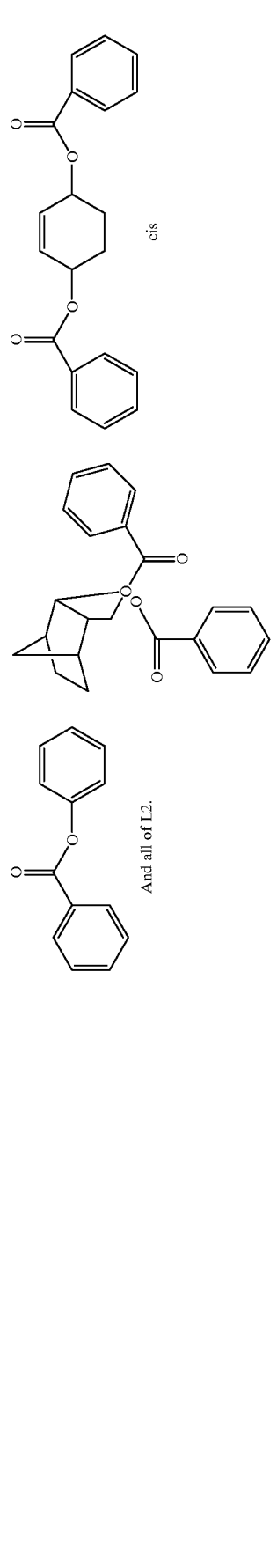

TABLE 3
LH3
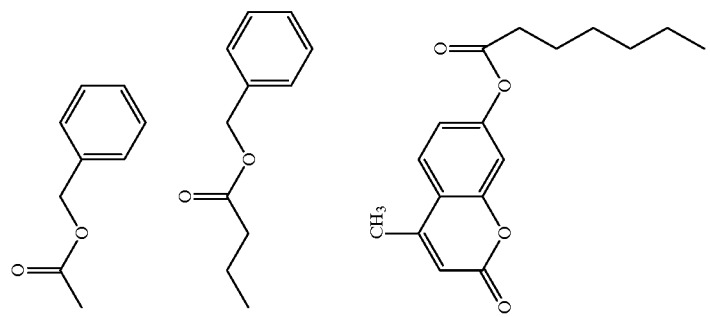
LI3
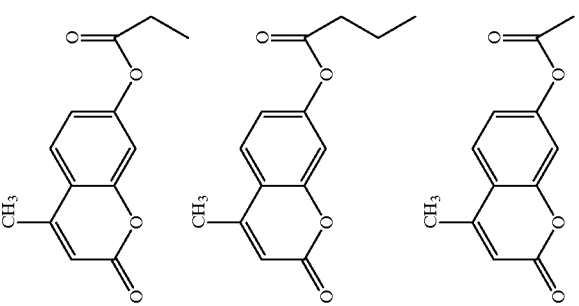
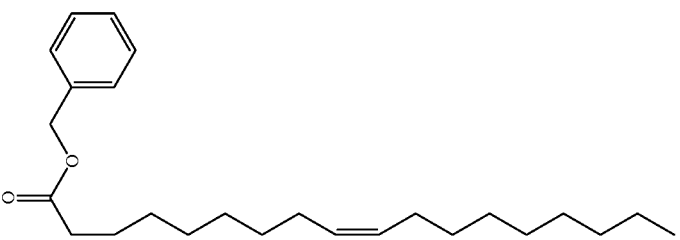
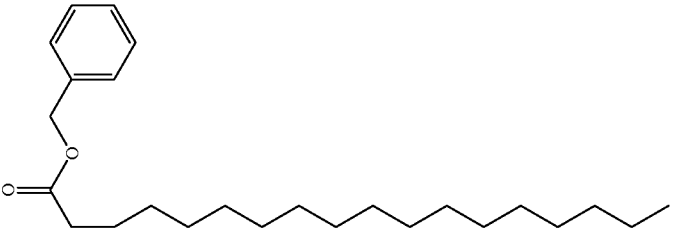
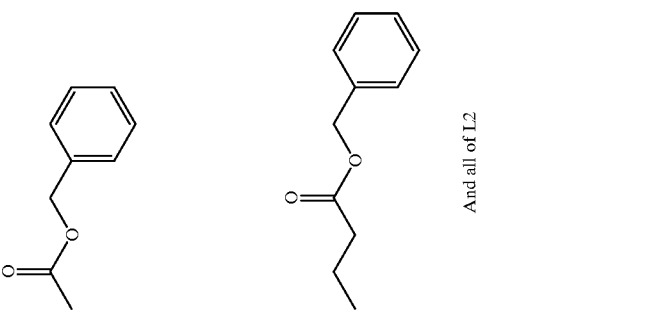
And all of L2

TABLE 3-continued
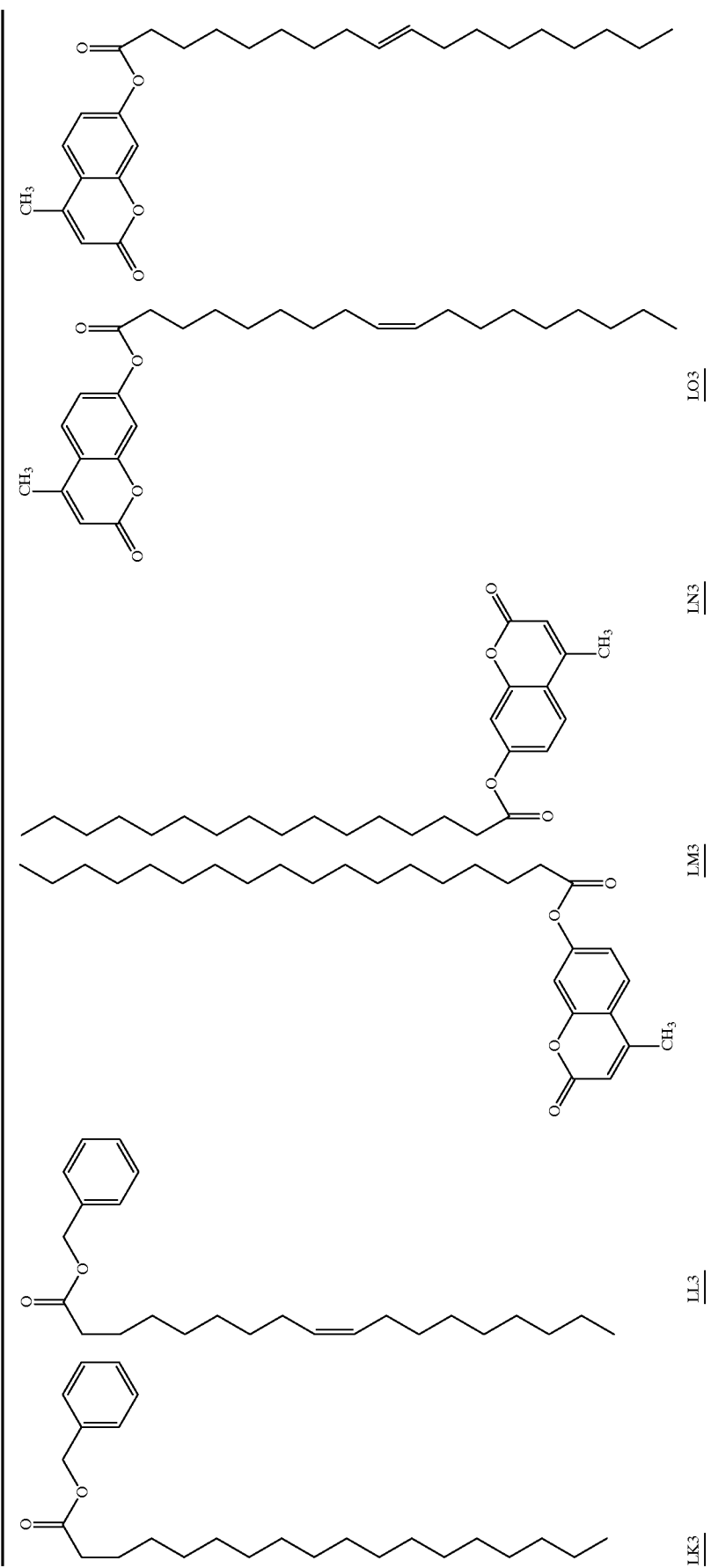

TABLE 3-continued
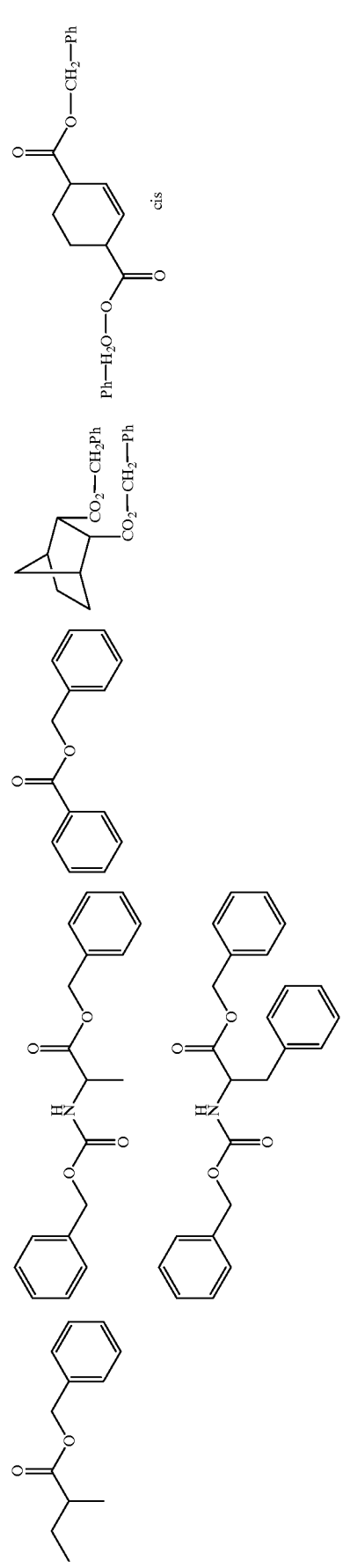

TABLE 4

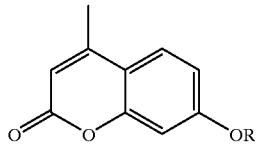

wherein R =

| | 4-methyl umbelliferone |
|---|---|
| G2 | β-D-galactose |
| | β-D-glucose |
| | β-D-glucuronide |
| GB3 | β-D-cellotrioside |
| | β-D-cellobiopyranoside |
| GC3 | β-D-galactose |
| | α-D-galactose |
| GD3 | β-D-glucose |
| | α-D-glucose |
| GE3 | β-D-glucuronide |
| GI3 | β-D-N,N-diacetylchitobiose |
| GJ3 | β-D-fucose |
| | β-L-fucose |
| | α-L-fucose |
| GK3 | β-D-mannose |
| | α-D-mannose |
| | non-Umbelliferyl substrates |
| GA3 | amylose [polyglucan α1,4 linkages], amylopectin [polyglucan branching α1,6 linkages] |
| GF3 | xylan [poly 1,4-D-xylan] |
| GG3 | amylopectin, pullulan |
| GH3 | sucrose, fructofuranoside |

TABLE 5

| COMPOUND | RELATIVE FLUORESCENCE |
|---|---|
| A | 60.6 |
| B | 73.6 |
| C | 100.0 |
| D | 84.2 |
| E | 29.1 |
| F | 5.4 |
| G | 7.1 |
| H | 0.9 |
| I | 0.0 |
| M | 9.4 |
| N | 0.5 |
| O | 0.5 |
| P | 4.0 |
| Q | 11.3 |

TABLE 5-continued

| COMPOUND | RELATIVE FLUORESCENCE |
|---|---|
| S | 0.6 |
| T | 0.1 |
| U | 0.3 |
| W | 0.2 |

What is claimed is:

1. A method for identifying clones of a recombinant library which express a protein with a desired characteristic, produced from DNA recovered from a plurality of species of organisms, comprising:

screening in the liquid phase a library of expression clones randomly produced from DNA recovered from the organisms, said screening being effected on expression products of said clones to thereby identify clones which express a protein with a desired characteristic.

2. The method of claim 1 wherein the DNA from the library of expression clones produced is gene cluster DNA.

3. The method of claim 1 wherein said protein is an enzyme.

4. A method of screening clones having DNA recovered from a plurality of species of organisms for a specified protein characteristic, which method comprises:

screening for a specified protein characteristic in a library of clones prepared by (i) recovering DNA from a DNA population derived from a plurality of species of organisms; and (ii) transforming a host cell with the recovered DNA to produce a library of clones which is screened for the specified protein characteristic.

5. The method of claim 4 wherein the recovered DNA is amplified.

6. The method of claim 4 wherein the recovered DNA is ligated into a vector.

7. The method of claim 6 wherein the vector into which the recovered DNA is ligated comprises at least one DNA sequence capable of regulating production of a detectable enzyme activity from said recovered DNA.

8. The method of claim 4 wherein the vector into which the recovered DNA has been ligated is used to transform a host cell.

9. The method of claim 4 a wherein the protein is an enzyme.

* * * * *